United States Patent
Yang et al.

(10) Patent No.: US 9,006,357 B2
(45) Date of Patent: Apr. 14, 2015

(54) CURABLE POLYSILOXANE COMPOSITION

(71) Applicant: 3M Innovative Properties Company, St. Paul, MN (US)

(72) Inventors: Yu Yang, Eden Prairie, MN (US); George G. I. Moore, Afton, MN (US); James T. Wolter, Oakdale, MN (US); Kanta Kumar, Woodbury, MN (US); Michael A. Semonick, White Bear Lake, MN (US); John L. Battiste, Northfield, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/368,332

(22) PCT Filed: Dec. 21, 2012

(86) PCT No.: PCT/US2012/071275
§ 371 (c)(1),
(2) Date: Jun. 24, 2014

(87) PCT Pub. No.: WO2013/106193
PCT Pub. Date: Jul. 18, 2013

(65) Prior Publication Data
US 2014/0342166 A1    Nov. 20, 2014

Related U.S. Application Data

(60) Provisional application No. 61/581,270, filed on Dec. 29, 2011.

(51) Int. Cl.
| | | |
|---|---|---|
| C09D 183/04 | (2006.01) |
| B05D 3/00 | (2006.01) |
| C07F 9/06 | (2006.01) |
| C07C 279/00 | (2006.01) |
| C07C 279/04 | (2006.01) |
| C09J 7/02 | (2006.01) |
| C08L 83/04 | (2006.01) |
| C08L 83/14 | (2006.01) |
| C08K 5/00 | (2006.01) |
| C08K 5/55 | (2006.01) |

(52) U.S. Cl.
CPC ............. *C09D 183/04* (2013.01); *C07F 9/065* (2013.01); *C07F 9/062* (2013.01); *C07C 279/00* (2013.01); *C07C 279/04* (2013.01); *C08K 5/0091* (2013.01); *C09J 7/025* (2013.01); *C08K 5/55* (2013.01); *C08L 83/04* (2013.01); *C08L 83/14* (2013.01); *C09J 2201/606* (2013.01); *C09J 2483/005* (2013.01); *B05D 3/007* (2013.01)

(58) Field of Classification Search
None
See application file for complete search history.

(56) References Cited

U.S. PATENT DOCUMENTS

| | | | |
|---|---|---|---|
| 2,708,289 A | 5/1955 | Collings | |
| 3,328,482 A | 6/1967 | Northrup et al. | |
| 3,338,847 A * | 8/1967 | Nitzsche et al. | ............... 521/126 |
| 3,445,417 A | 5/1969 | Layne et al. | |
| 3,628,996 A | 12/1971 | Weber | |
| 3,969,543 A | 7/1976 | Roberts et al. | |
| 4,181,752 A | 1/1980 | Martens et al. | |
| 4,262,157 A | 4/1981 | Hori et al. | |
| 4,269,963 A | 5/1981 | Homan et al. | |
| 4,489,199 A | 12/1984 | Wengrovius | |
| 4,515,932 A | 5/1985 | Chung | |
| 4,612,134 A * | 9/1986 | Pierce et al. | ..................... 252/75 |
| 4,761,443 A | 8/1988 | Lopes | |
| 5,183,873 A * | 2/1993 | Viksne | ............................ 528/16 |
| 5,219,958 A | 6/1993 | Noomen et al. | |
| 5,229,212 A | 7/1993 | Reed | |
| 5,286,815 A | 2/1994 | Leir et al. | |
| 5,371,162 A | 12/1994 | Konings et al. | |
| 5,403,909 A | 4/1995 | Rubinsztajn | |
| 5,484,873 A | 1/1996 | Johnson | |
| 5,688,888 A | 11/1997 | Burkus, II et al. | |
| 5,789,460 A | 8/1998 | Harkness et al. | |
| 5,820,944 A | 10/1998 | Harkness et al. | |
| 5,866,222 A | 2/1999 | Seth et al. | |
| 5,891,529 A | 4/1999 | Harkness et al. | |

(Continued)

FOREIGN PATENT DOCUMENTS

| | | |
|---|---|---|
| EP | 0 444 633 A2 | 9/1991 |
| JP | 61022094 A | 1/1986 |

(Continued)

OTHER PUBLICATIONS

Arenivar, "Bismuth Carboxylates for Polyurethane Catalysis," *Polyurethanes* 89, Proceedings of the SPI 32$^{nd}$ Annual Technical Marketing Conference, Oct. 1-4, 1989, pp. 623-627.

(Continued)

*Primary Examiner* — Robert S Loewe
(74) *Attorney, Agent, or Firm* — Eric E. Silverman

(57) ABSTRACT

A curable composition comprises (a) at least one polyorganosiloxane, fluorinated polyorganosiloxane, or combination thereof comprising reactive silane functionality comprising at least two hydroxysilyl moieties; (b) at least one polyorganosiloxane, fluorinated polyorganosiloxane, or combination thereof comprising reactive silane functionality comprising at least two hydrosilyl moieties; and (c) a catalyst composition comprising (1) at least one base selected from amidines, guanidines, phosphazenes, proazaphosphatranes, and combinations thereof, and (2) at least one Lewis acid; wherein at least one of the components (a) and (b) has an average reactive silane functionality of at least three.

20 Claims, No Drawings

(56) References Cited

U.S. PATENT DOCUMENTS

| | | | |
|---|---|---|---|
| 5,895,794 A * | 4/1999 | Berg et al. | 523/217 |
| 6,013,682 A | 1/2000 | Dalle et al. | |
| 6,096,483 A | 8/2000 | Harkness et al. | |
| 6,124,371 A | 9/2000 | Stanssens et al. | |
| 6,136,996 A | 10/2000 | Rubinsztajn et al. | |
| 6,166,207 A | 12/2000 | Friedrich et al. | |
| 6,204,350 B1 | 3/2001 | Liu et al. | |
| 6,235,832 B1 | 5/2001 | Deng et al. | |
| 6,277,986 B1 | 8/2001 | Hall-Goulle et al. | |
| 6,551,761 B1 | 4/2003 | Hall-Goulle et al. | |
| 6,740,717 B2 | 5/2004 | Moren | |
| 6,777,512 B1 | 8/2004 | Sonnenschein et al. | |
| 6,780,484 B2 | 8/2004 | Kobe et al. | |
| 6,805,933 B2 | 10/2004 | Patel et al. | |
| 6,835,422 B2 | 12/2004 | Kobe et al. | |
| 7,064,173 B2 | 6/2006 | Rubinsztajn et al. | |
| 7,148,370 B1 | 12/2006 | Rubinsztajn et al. | |
| 7,300,747 B2 | 11/2007 | Okazaki et al. | |
| 7,332,541 B2 | 2/2008 | Schindler et al. | |
| 7,482,391 B1 | 1/2009 | Cross et al. | |
| 7,538,104 B2 | 5/2009 | Baudin et al. | |
| 8,470,899 B2 * | 6/2013 | Maliverney | 521/129 |
| 2001/0037008 A1 | 11/2001 | Sherman et al. | |
| 2003/0139287 A1 | 7/2003 | Deforth et al. | |
| 2004/0242867 A1 | 12/2004 | Baudin et al. | |
| 2006/0014844 A1 | 1/2006 | Lim et al. | |
| 2006/0041097 A1 * | 2/2006 | Herrwerth et al. | 528/14 |
| 2006/0111505 A1 | 5/2006 | Schindler et al. | |
| 2006/0247341 A1 | 11/2006 | Hsieh et al. | |
| 2006/0293172 A1 * | 12/2006 | Rubinsztajn et al. | 502/155 |
| 2007/0004017 A1 * | 1/2007 | Bramucci et al. | 435/136 |
| 2009/0171025 A1 | 7/2009 | Matsushita et al. | |
| 2010/0036049 A1 | 2/2010 | Matsushita et al. | |
| 2010/0041810 A1 | 2/2010 | Wakabayashi et al. | |
| 2010/0168454 A1 | 7/2010 | Jiang et al. | |
| 2011/0028585 A1 | 2/2011 | Shiraishi et al. | |
| 2011/0098392 A1 | 4/2011 | Barrandon et al. | |
| 2011/0098420 A1 * | 4/2011 | Takizawa et al. | 525/477 |
| 2012/0258269 A1 * | 10/2012 | Gehringer et al. | 428/36.9 |
| 2013/0101840 A1 | 4/2013 | Yang et al. | |
| 2013/0101841 A1 | 4/2013 | Yang et al. | |
| 2013/0102728 A1 | 4/2013 | Yang et al. | |
| 2013/0157059 A1 * | 6/2013 | Ogawa | 428/414 |
| 2013/0178553 A1 | 7/2013 | Yang et al. | |

FOREIGN PATENT DOCUMENTS

| | | |
|---|---|---|
| WO | WO2004/022618 A1 | 3/2004 |
| WO | WO2007/149422 A2 | 12/2007 |
| WO | WO 2009/122664 A1 | 10/2009 |
| WO | WO 2010/146254 A1 | 12/2010 |
| WO | WO 2010/149869 A1 | 12/2010 |
| WO | WO 2012/003152 A1 | 1/2012 |
| WO | WO 2013/096554 A1 | 6/2013 |
| WO | WO 2013/101477 A1 | 7/2013 |
| WO | WO 2013/101742 A1 | 7/2013 |

OTHER PUBLICATIONS

Fournier et al., "1,8-Diazabicyclo[5.4.0]undec-7-ene (DBU) as Ligand for Atom Transfer Radical Polymerization (ATRP)," *European Polymer Journal*, vol. 41 (2005), pp. 1576-1581.

Hartman et al., Bis- and Tris(Amidine)Fluoroboron Cations and Mixed Tetrahaloborate Anions: NMR Studies of Mixed Boron Trihalide Adduct Redistribution Reactions Involving Amidines as Strong Nitrogen Bases, *Can. J. Chem.*, vol. 74, (1996), pp. 2131-2142.

Kim et al., "Cure Kinetics of Biphenyl Epoxy Resin System Using Latent Catalysts," *Journal of Applied Polymer Science*, vol. 81, (2001), pp. 2711-2720.

Li et al., "Novel Organic-Inorganic Hybrid Coordination Polymer [(DBU-H)(PbI$_3$)]$_n$: Synthesis, Crystallographic Structure and Quantum Chemical Investigation," *Chinese Journal of Chemistry*, vol. 23, (2005), pp. 1391-1396.

Pérez et al., "Efficient and Clean Synthesis of N-alkyl Carbamates by Transcarboxylation and O-alkylation Coupled Reactions Using a DBU-CO$_2$ Zwitterionic Carbamic Complex in Aprotic Polar Media," *Tetrahedron Letters*, vol. 43, (2002), pp. 4091-4093.

Del Sole et al., "First Evidence of Formation of Stable DBU Zn-Phthalocyanine Complexes: Synthesis and Characterization," *Journal of Porphyrins and Phthalocyanines*, vol. 9, (2005), pp. 519-527.

Org. Lett. 9, No. 1, (2007), pp. 1-169.

E. Lukevics and M. Dzintara, "Silylation of Hydroxyl-Containing Compounds with Aryl and Heteroaryl-Hydrosilanes in the Presence of Amines," Journal of Organometallic Chemistry 271, pp. 307-317 (1984).

Kanji et al., "Quaternary Ammonium Salt as DBU-Generating Photobase Generator", Journal of Photopolymer Science and Technology, 19(1), 81-84 (Jan. 1, 2006).

Chemtob et al., "UV-Activated Silicone Oligomer Cross-Linking Through Photoacid and Photobase Organocatalysts," *J. Appl. Polym. Sci.* 2013, 6 pages.

Suyama et al., "Photobase Generators: Recent Progress and Application Trend in Polymer Systems," *Progress in Polymer Science* 34 (2009) 194-209.

"Silicon Compounds: Silanes and Silicones," Second Edition, edited by B. Arkles and G. Larson, Gelest, Inc. (2008).

"Peel Adhesion of Pressure Sensitive Tape," Pressure Sensitive Tape Council PSTC-101 Method D (Rev May 2007).

International Search Report for PCT Application No. PCT/US2012/071275, filed Dec. 21, 2012, 4 pp.

* cited by examiner

CURABLE POLYSILOXANE COMPOSITION

STATEMENT OF PRIORITY

This application claims the priority of U.S. Provisional Application No. 61/581,270, filed Dec. 29, 2011; the contents of which are hereby incorporated by reference.

FIELD

This invention relates to curable coating compositions comprising reactive silane functionality and, in other aspects, to processes for coating the compositions and articles prepared thereby.

BACKGROUND

Moisture-curable polysiloxane compositions cure in the presence of moisture to form crosslinked materials such as release coatings and surface treatments that are useful in many industries. For example, a polysiloxane or fluorinated polysiloxane is often selected to provide moisture-curable release coatings suitable for use with pressure-sensitive adhesives. The moisture for curing is typically obtained from the atmosphere or from a substrate to which the composition has been applied, although it can also be added to the composition (for example, to enable curing in depth or in confinement).

Moisture-curable polysiloxane compositions usually comprise siloxane polymers having groups (for example, alkoxysilyl or acyloxysilyl moieties) that can react in the presence of moisture to form cured (that is, crosslinked) materials. Moisture-curable compositions comprising alkoxysilyl or acyloxysilyl functionality typically cure in two reactions. In the first reaction, the alkoxysilyl or acyloxysilyl groups hydrolyze in the presence of moisture and a catalyst to form silanol compounds having hydroxysilyl groups. In the second reaction, the hydroxysilyl groups condense with other hydroxysilyl, alkoxysilyl, or acyloxysilyl groups in the presence of a catalyst to form —Si—O—Si— linkages. The two reactions occur essentially simultaneously upon generation of the silanol compound. Commonly used catalysts for the two reactions include Bronsted and Lewis acids. A single material can catalyze both reactions.

Preferably, the hydrolysis and condensation reactions proceed quickly after the moisture-curable composition has been applied, for example, to a substrate. At the same time, however, the reactions must not occur prematurely, for example, during processing or storage.

A good balance between these properties is often difficult to obtain, as rapid reactivity and storage stability are opposite properties to each other. For example, highly active catalysts such as tetraalkyl titanate esters rapidly accelerate the moisture-curing reaction but, at the same time, can make it difficult to process the materials without risking premature gelation in feed tanks, coating equipment, and other manufacturing and handling apparatus. Control of the amount of moisture can be critical, with too little moisture potentially resulting in slow or incomplete cure and too much moisture resulting in premature cure.

A variety of approaches have been used for providing moisture-curable compositions that have acceptable cure rates without processing and storage difficulties. For example, two-part systems have been developed (one part comprising a functional siloxane polymer and the other part comprising a catalyst), with the two parts being mixed immediately prior to use. While this approach has been useful in small-scale applications, it has been less efficient for large-scale manufacturing, where delays caused by having to mix the two parts have been undesirable. Furthermore, coating operations must be completed expeditiously before the composition cures in the pot, and this has been difficult when working with large surface area substrates or a large volume of composition.

Ammonium salt catalysts have been developed that are inactive until heated sufficiently to liberate an acid compound that initiates the moisture curing reaction. Liberation of the acid also generates an amine, however, that must be removed by evaporation. In addition, the heat used to activate the catalyst can damage heat-sensitive substrates onto which the composition has been applied.

Other materials (for example, onium salts such as sulfonium and iodonium salts) have been used to generate acid species in situ upon irradiation (for example, irradiation with ultraviolet light). Such materials have not required heat activation and therefore have enabled the use of heat-sensitive substrates without damage (and without the production of undesirable species requiring removal), but the materials have been relatively expensive, have exhibited cure inhibition on some substrates, and have required moisture control and the use of coating equipment with irradiation capability.

Conventional tin catalysts such as dibutyl tin dilaurate can provide stable curable polysiloxane compositions that can be processed and coated without premature gelation. In addition to typical moisture-curable systems, it has been found that curable compositions comprising dual reactive silane functionality in the form of hydrosilyl and hydroxysilyl groups (dehydrogenatively-curable systems) can be cured by using tin catalysts. The compositions have been widely used for pressure-sensitive adhesive and mold release applications but have sometimes suffered from relatively short pot lives. In addition, the use of tin catalysts is becoming particularly problematic because the organotin compounds generally employed as catalysts are now considered to be toxicologically objectionable.

Acceleration of cure has been achieved by the use of compounds such as diorganosulfoxides, imidazoles, and amines (including amidines and substituted guanidines) in combination with tin catalysts (and, in some cases, amine compounds alone) in various silicone compositions (including room temperature vulcanizing silicone compositions and dehydrogenatively-cured silicone compositions). Amine compounds including amidines have also been proposed for use in the absence of tin catalysts for curing moisture-curable, silyl-functional organic polymers, but practical curability of alkoxysilyl-functional organic polymers and acceptable adhesion to substrates were achieved only with strongly basic amines (those exhibiting a pH of at least 13.4 in aqueous solution).

Complexes of at least one Lewis acid and at least one nitrogen-containing, organic base have been used as catalysts in various types of reactions including hydrogenation of double bonds, reaction of compounds with isocyanate and hydroxyl functional groups to form urethane and/or polyurethane, atom transfer radical polymerization of (meth)acrylates and styrene, curing of biphenyl epoxy-phenol resin systems and other thermosettable compositions, decarboxylation of carboxylic acids, and synthesis of N-alkyl carbamates. The use of such complexes in the condensation curing (including dehydrogenative or dehydrocondensation curing) of silicone compositions, however, is believed not to have been reported.

SUMMARY

Thus, we recognize that there exists an ongoing need for curable polysiloxane compositions that can provide acceptable cure rates without significant processing and storage difficulties (for example, due to premature gelation). Preferably, these compositions will be efficiently processable (for example, without the need for mixing of a two-part system prior to cure), will employ catalysts that do not generate species requiring removal, and/or will not require high-temperature activation (so as to enable curing at relatively low temperatures and/or the use of heat-sensitive substrates). Ideally, the compositions will employ catalysts that are relatively non-toxic, provide compositions that are relatively stable in solution but relatively fast-curing upon drying, effective in relatively low concentrations, and/or effective under relatively low (or no) moisture conditions.

Briefly, in one aspect, this invention provides a curable polysiloxane composition comprising dual reactive silane functionality. The composition comprises
- (a) at least one polyorganosiloxane, fluorinated polyorganosiloxane, or combination thereof comprising reactive silane functionality comprising at least two hydroxysilyl moieties (that is, monovalent moieties comprising a hydroxyl group bonded directly to a silicon atom);
- (b) at least one polyorganosiloxane, fluorinated polyorganosiloxane, or combination thereof comprising reactive silane functionality comprising at least two hydrosilyl moieties (that is, monovalent moieties comprising a hydrogen atom bonded directly to a silicon atom); and
- (c) a catalyst composition comprising (1) at least one base selected from amidines, guanidines, phosphazenes, proazaphosphatranes, and combinations thereof, and (2) at least one Lewis acid;

wherein at least one of components (a) and (b) has an average reactive silane functionality of at least three (that is, component (a) has at least three hydroxysilyl moieties (on average), component (b) has at least three hydrosilyl moieties (on average), or both).

Components (a) and (b) preferably comprise at least one polyorganosiloxane (more preferably, at least one polyalkylsiloxane (that is, at least one polydialkylsiloxane, polyalkyl (hydro)siloxane, or a combination thereof); most preferably, at least one polymethylsiloxane (that is, at least one polydimethylsiloxane, polymethyl(hydro)siloxane, or a combination thereof)) having the above-specified reactive silane functionalities, respectively.

Preferably, component (a) is hydroxyl-endblocked, so as to comprise two terminal hydroxysilyl moieties (on average). The base preferably comprises at least one amidine or guanidine (most preferably, 1,8-diazabicyclo[5.4.0]-7-undecene (DBU)). Optionally, the curable polysiloxane composition further comprises at least one carboxylic acid or anhydride. The curable polysiloxane composition preferably further comprises at least one solvent (for example, an aprotic organic solvent such as heptane).

It has been discovered that, unlike standard amine bases such as 4,4'-trimethylenebis(1-methylpiperidine) (which are ineffective), the above-described bases can effectively catalyze the curing (apparently, by dehydrocondensation) of polysiloxane compositions comprising reactive silane functionality in the form of hydrosilyl and hydroxysilyl moieties. The bases can provide relatively rapid cure (for example, upon removal of solvent curing can occur within periods of time as short as about 1 minute) even at temperatures as low as ambient (for example, about 23° C.), without the need for heat activation, and can be effective in relatively small amounts (for example, at concentrations as low as about 0.5 weight percent or less, based upon the total weight of components (a), (b), and (c)). Thus, polysiloxane compositions comprising the bases can be suitable for use in high speed coating and curing operations in an industrial setting, without the need for addition of heat. In spite of such effective curability, the compositions can exhibit relatively good storage stability (for example, for a period of days in a closed container) and/or relatively long pot life (for example, on the order of 8 hours or more) in a variety of solvents (for example, heptane, methyl ethyl ketone, or a combination thereof), without the need for mixing of a two-part system immediately prior to use.

It has also been discovered, however, that the catalytic activity or curing performance of the bases surprisingly can be further enhanced and/or controlled by the addition of Lewis acid(s). When a catalyst composition comprising at least one base and at least one Lewis acid is used, somewhat higher processing temperatures can be utilized (for example, without significant curing occurring below temperatures of about 50° C.) and/or byproduct formation and outgassing can be reduced or even essentially eliminated (for example, byproducts resulting from side reactions involving one or both polysiloxane components). Thus, the addition of Lewis acid surprisingly can further extend bath life and/or increase the degree of cure that can be achieved, resulting in lower levels of extractables upon curing. These unexpected improvements can be even further enhanced by the optional inclusion of at least one carboxylic acid or anhydride in the curable polysiloxane composition.

In surprising contrast with prior art compositions, the catalyst compositions can be effective in the curable polysiloxane composition of the invention in the substantial absence of other condensation catalysts and/or in the substantial absence of moisture. The catalyst compositions can be used as substitutes for conventional tin catalysts to provide tin-free, curable polysiloxane compositions, without the need for changes in the nature of the polysiloxane components of conventional tin-cured polysiloxane compositions (for example, release coating compositions such as Syl-Off™ 292 coating composition, available from Dow Corning Corporation, Midland, Mich.). Unlike the conventional tin catalysts, at least some of the catalyst compositions (for example, DBU and zinc alkanoate) are relatively non-toxic and therefore suitable for use in preparing relatively environmentally friendly or "green" polysiloxane compositions.

The curable polysiloxane composition of the invention can be cured to provide crosslinked networks having properties that can be tailored to the requirements of various different applications (for example, by varying the natures, relative amounts, and/or degrees of reactive silane functionality of starting components (a) and/or (b)). Thus, the curable polysiloxane composition can be used to provide coatings having a variety of surface properties for use in numerous coating applications (for example, use as release coatings for pressure-sensitive adhesives, protective coatings, water- and/or oil-repellent coatings or surface treatments, and the like). The curable polysiloxane composition of the invention can be particularly useful in relatively sensitive applications requiring careful and/or tailored control of surface properties (for example, release coating applications), as at least some embodiments of the curable polysiloxane compositions comprise catalyst compositions (for example, DBU and triethylborate) that do not appear to produce species that remain after curing, possibly because such species are sufficiently volatile to be evaporated from the composition during processing, thereby leaving essentially no catalyst contamination in the cured material (in contrast with the tin contamination of conventional tin catalysts, which can be particularly problematic in the area of electronics).

In view of the foregoing, at least some embodiments of the curable polysiloxane composition of the invention meet the above-described, ongoing need for curable compositions that can provide acceptable cure rates without significant processing and storage difficulties (for example, being relatively stable in solution but relatively fast-curing upon drying), while also being efficiently processable (for example, without the need for mixing of a two-part system prior to cure, for contaminant removal, and/or for high-temperature activation). At least some embodiments of the curable polysiloxane composition also employ catalysts that are relatively non-toxic, while being effective in relatively low concentrations and/or under relatively low (or no) moisture conditions.

In another aspect, this invention also provides a coating process comprising (a) providing the above-described curable polysiloxane composition of the invention;

(b) providing at least one substrate having at least one major surface;

(c) applying the curable polysiloxane composition to at least a portion of at least one major surface of the substrate; and (d) allowing or inducing the curable polysiloxane composition to cure to form a coating.

In yet another aspect, this invention provides an article comprising at least one substrate having at least one major surface, the substrate bearing, on at least a portion of at least one major surface, a coating prepared by the above-described coating process.

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

As used herein, the term "and/or" means one or all of the listed elements or a combination of any two or more of the listed elements.

The words "preferred" and "preferably" refer to embodiments of the invention that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The term "comprises" and variations thereof do not have a limiting meaning where these terms appear in the description and claims.

As used herein, "a," "an," "the," "at least one," and "one or more" are used interchangeably.

The above "Summary of the Invention" section is not intended to describe every embodiment or every implementation of the invention. The detailed description that follows more particularly describes illustrative embodiments. Throughout the detailed description, guidance is provided through lists of examples, which examples can be used in various combinations. In each instance, a recited list serves only as a representative group and should not be interpreted as being an exclusive list.

Definitions

As used in this patent application:

"catenated heteroatom" means an atom other than carbon (for example, oxygen, nitrogen, or sulfur) that replaces one or more carbon atoms in a carbon chain (for example, so as to form a carbon-heteroatom-carbon chain or a carbon-heteroatom-heteroatom-carbon chain);

"cure" means conversion to a crosslinked polymer network (for example, through catalysis);

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated;

"heteroorganic" means an organic group or moiety (for example, an alkyl or alkylene group) containing at least one heteroatom (preferably, at least one catenated heteroatom);

"hydrosilyl" refers to a monovalent moiety or group comprising a silicon atom directly bonded to a hydrogen atom (for example, the hydrosilyl moiety can be of formula —Si(R)$_{3-p}$(H)$_p$, where p is an integer of 1, 2, or 3 and R is a hydrolyzable or non-hydrolyzable group (preferably, non-hydrolyzable) such as alkyl or aryl);

"hydroxysilyl" refers to a monovalent moiety or group comprising a silicon atom directly bonded to a hydroxyl group (for example, the hydroxysilyl moiety can be of formula —Si(R)$_{3-p}$(OH)$_p$ where p is an integer of 1, 2, or 3 and R is a hydrolyzable or non-hydrolyzable group (preferably, non-hydrolyzable) such as alkyl or aryl);

"Lewis acid" means a molecular entity (and the corresponding chemical species) that is an electron-pair acceptor and therefore able to react with a Lewis base to form a Lewis adduct by sharing the electron pair furnished by the Lewis base;

"mercapto" means a monovalent group or moiety of formula —SH;

"oligomer" means a molecule that comprises at least two repeat units and that has a molecular weight less than its entanglement molecular weight; such a molecule, unlike a polymer, exhibits a significant change in properties upon the removal or addition of a single repeat unit;

"oxy" means a divalent group or moiety of formula —O—; and

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

Component (a)

Polysiloxanes suitable for use as component (a) of the curable polysiloxane composition of the invention include polyorganosiloxanes, fluorinated polyorganosiloxanes, and combinations thereof (preferably, polyorganosiloxanes; more preferably, polydialkylsiloxanes) comprising reactive silane functionality comprising at least two hydroxysilyl moieties (that is, monovalent moieties comprising a hydroxyl group bonded directly to a silicon atom). The polysiloxanes can be oligomers, polymers, or a combination thereof. Preferably, the polysiloxanes are polymers, which can be linear, branched, or cyclic. Useful polymers include those that have random, alternating, block, or graft structures, or a combination thereof.

The molecular weight and the reactive silane functionality of component (a) (including the number and nature of the hydroxysilyl moieties) of the polysiloxanes can vary widely, depending upon, for example, the molecular weight and the reactive silane functionality of component (b) and the properties desired for the curable and/or cured composition. At least one of components (a) and (b) has an average reactive silane functionality of at least three, however (that is, component (a) has at least three hydroxysilyl moieties (on average), component (b) has at least three hydrosilyl moieties (on average), or both), so as to enable the formation of a crosslinked network.

Preferably, the polyorganosiloxanes, fluorinated polyorganosiloxanes, and combinations thereof used for component (a) are hydroxyl-endblocked, so as to comprise two terminal hydroxysilyl moieties (on average). The polysiloxanes preferably have a weight average molecular weight of about 150 to about 1,000,000 (more preferably, about 1,000 to about 1,000,000).

A preferred class of useful polysiloxanes includes those that can be represented by the following general formula:

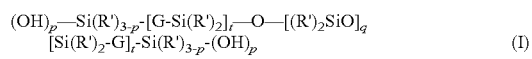
$$[Si(R')_2\text{-}G]_t\text{-}Si(R')_{3-p}\text{-}(OH)_p \quad (I)$$

wherein each p is independently an integer of 1, 2, or 3 (preferably, 1); each G is independently a divalent linking group; each R' is independently selected from alkyl, alkenyl, fluoroalkyl, aryl, fluoroaryl, cycloalkyl, fluorocycloalkyl, heteroalkyl, heterofluoroalkyl, heteroaryl, heterofluoroaryl, heterocycloalkyl, heterofluorocycloalkyl, and combinations thereof; q is an integer of 0 to about 15,000 (preferably, about 20 to about 15,000); and each t is independently an integer of 0 or 1 (preferably, 0). Preferably, each R' is independently selected from alkyl (preferably, having 1 to about 8 carbon atoms), fluoroalkyl (preferably, having 3 to about 8 carbon atoms; more preferably, $R_fC_2H_4$—, wherein $R_f$ is a fluorinated or perfluorinated alkyl group having 1 to about 6 carbon atoms (preferably, 1 to about 6 carbon atoms)), aryl, and combinations thereof (with alkyl being most preferred). More preferably, each R' is independently selected from methyl, $C_4F_9C_2H_4$—, $C_6F_{13}C_2H_4$—, $CF_3C_2H_4$—, phenyl, $C_6H_5C_2H_4$—, and combinations thereof (even more preferably, methyl, $CF_3C_2H_4$—, phenyl, $C_4F_9C_2H_4$—, and combinations thereof; most preferably, methyl). Each divalent linking group, G, is preferably independently selected from oxy, alkylene, arylene, heteroalkylene, heteroarylene, cycloalkylene, heterocycloalkylene, and combinations thereof (more preferably, selected from oxy, alkylene, arylene, and combinations thereof). Heteroatoms (in G and/or R') can include oxygen, sulfur, nitrogen, phosphorus, and combinations thereof (preferably, oxygen, sulfur, and combinations thereof; more preferably, oxygen). G can contain fluorine, provided that it is separated from silicon by at least two carbon atoms.

Preferred polysiloxanes include hydroxyl-endblocked polydimethylsiloxane homopolymer, as well as hydroxyl-endblocked copolymers comprising dimethylsiloxane units and up to about 40 or 50 mole percent of other units selected from dialkylsiloxane units, (alkyl)(methyl)siloxane units, and (alkyl)(phenyl)siloxane units wherein each alkyl group is independently selected from alkyl groups having two to about 8 carbon atoms (for example, hexyl), di(fluoroalkyl)siloxane units, (fluoroalkyl)(methyl)siloxane units, and (fluoroalkyl)(phenyl)siloxane units wherein each fluoroalkyl group is independently selected from fluoroalkyl groups having 3 to about 8 carbon atoms (for example, trifluoropropyl or nonafluorohexyl), diphenylsiloxane units, and combinations thereof.

The polysiloxanes useful as component (a) can be used in the curable composition of the invention singly or in the form of mixtures of different polysiloxanes. Sometimes mixtures can be preferred. A preferred composition for use as component (a) comprises a mixture of (1) at least one polyorganosiloxane, fluorinated polyorganosiloxane, or combination thereof (preferably, at least one polyorganosiloxane) having a weight average molecular weight in the range of about 300,000 to about 1,000,000 (more preferably, about 400,000 to about 900,000; most preferably, about 500,000 to about 700,000) and (2) at least one polyorganosiloxane, fluorinated polyorganosiloxane, or combination thereof (preferably, at least one polyorganosiloxane) having a weight average molecular weight in the range of about 150 to about 150,000 (more preferably, about 10,000 to about 120,000; most preferably, about 10,000 to about 15,000). The relative amounts of component (1) and component (2) and their molecular weights can be selected for release applications according to the nature of the adhesive (or other material) to be utilized and the level of release desired.

For example, for mold release applications, the weight ratio of the former polysiloxane to the latter polysiloxane can range from about 3:1 to about 19:1 (preferably, about 4:1 to about 9:1; more preferably, about 6:1). For pressure sensitive adhesive (PSA) release applications, the weight ratio of the former polysiloxane to the latter polysiloxane can range, for example, from about 2:1 to about 1:10 (preferably, about 1:1 to about 1:6; more preferably, about 1:2 to about 1:4).

The polysiloxanes suitable for use as component (a) can be prepared by known synthetic methods and many are commercially available. For example, the hydroxysilyl-functional components of Syl-Off™ 292 coating composition (available from Dow Corning Corporation, Midland, Mich.) are preferred polysiloxanes, and other useful polysiloxanes of varying molecular weight can be obtained from Gelest, Inc., Morrisville, Pa. (see, for example, the polysiloxanes described in *Silicon Compounds: Silanes and Silicones*, Second Edition, edited by B. Arkles and G. Larson, Gelest, Inc. (2008)).

Component (b)

Polysiloxanes suitable for use as crosslinker component (b) of the curable composition of the invention include polyorganosiloxanes, fluorinated polyorganosiloxanes, and combinations thereof (preferably, polyorganosiloxanes; more preferably, polyalkyl(hydro)siloxanes) comprising reactive silane functionality comprising at least two hydrosilyl moieties (that is, monovalent moieties comprising a hydrogen atom bonded directly to a silicon atom). The polysiloxanes can be small molecules, oligomers, polymers, or a combination thereof. Preferably, the polysiloxanes are polymers. The polysiloxanes can be linear, branched, or cyclic. Useful polymers include those that have random, alternating, block, or graft structures, or a combination thereof.

The molecular weight and the reactive silane functionality of component (b) (including the number and nature of the hydrosilyl moieties) can vary widely, depending upon, for example, the molecular weight and the reactive silane functionality of component (a) and the properties desired for the curable and/or cured composition. Preferably, component (b) has an average reactive silane functionality of at least three (so as to enable the formation of a crosslinked network when component (a) is hydroxyl-endblocked). The polysiloxanes preferably have a weight average molecular weight of about 100 to about 100,000.

A preferred class of polysiloxanes includes those that can be represented by the following general formula:

wherein R' is as defined above for Formula (I); each R" is independently hydrogen (hydro) or R'; r is an integer of 0 to about 150 (preferably, 0 to about 100; more preferably, 0 to about 20); and s is an integer of 2 to about 150 (preferably, about 5 to about 100; more preferably, about 20 to about 80). Most preferably, both R" and R' are methyl, r is 0, and/or s is about 40.

Preferred hydride-functional polysiloxanes include those comprising polymethyl(hydro)siloxane homopolymer, as well as those comprising copolymer(s) comprising methyl (hydro)siloxane units and up to about 40 or 50 mole percent of other units selected from dialkylsiloxane units, (alkyl)(methyl)siloxane units, and (alkyl)(phenyl)siloxane units wherein each alkyl group is independently selected from alkyl groups having two to about 8 carbon atoms (for example, hexyl), di(fluoroalkyl)siloxane units, (fluoroalkyl)(methyl)siloxane units, and (fluoroalkyl)(phenyl)siloxane units wherein each fluoroalkyl group is independently selected from fluoroalkyl groups having 3 to about 8 carbon atoms (for example, trifluoropropyl or nonafluorohexyl), diphenylsiloxane units, and combinations thereof. Although homopolymer is often preferred, copolymers can be preferred for some applications.

The polysiloxanes useful as component (b) can be used in the curable composition of the invention singly or in the form of mixtures of different polysiloxanes. The polysiloxanes can be prepared by known synthetic methods and many are commercially available. For example, Syl-Off™ Q2-7560 crosslinker, Syl-Off™ 7678 crosslinker, and the hydrosilyl-functional component (for example, Syl-Off™ 7048 crosslinker) of Syl-Off™ 292 and Syl-Off™ 294 coating compositions (all available from Dow Corning Corporation, Midland, Mich.) are preferred polysiloxanes, and other useful polysiloxane crosslinkers of varying molecular weight can be obtained from Gelest, Inc., Morrisville, Pa. (see, for example, the polysiloxanes described in Silicon Compounds: Silanes and Silicones, Second Edition, edited by B. Arkles and G. Larson, Gelest, Inc. (2008)).

Component (c)

Bases suitable for use in component (c) (the catalyst composition) of the curable composition of the invention include amidines, guanidines (including substituted guanidines such as biguanides), phosphazenes, proazaphosphatranes (also known as Verkade's bases), and combinations thereof. Self-protonatable forms of the bases (for example, aminoacids such as arginine) generally are less suitable and therefore excluded, as such forms are self-neutralized and therefore insoluble in the curable composition. Preferred bases include amidines, guanidines, and combinations thereof (more preferably, amidines and combinations thereof; most preferably, cyclic amidines and combinations thereof).

It has been discovered that the bases of the listed structural classes can effectively catalyze reaction between components (a) and (b), as described above. The bases can be used in the curable composition singly (individually) or in the form of mixtures of one or more different bases (including bases from different structural classes). If desired, the base(s) can be present in photolatent form (for example, in the form of an activatable composition that, upon exposure to radiation or heat, generates the base(s) in situ).

Useful amidines include those that can be represented by the following general formula:

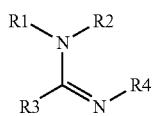

(III)

wherein R1, R2, R3, and R4 are each independently selected from hydrogen, monovalent organic groups, monovalent heteroorganic groups (for example, comprising nitrogen, oxygen, phosphorus, silicon, or sulfur in the form of groups or moieties that are preferably bonded through a carbon atom and that do not contain acid functionality such as carboxylic or sulfonic), and combinations thereof; and wherein any two or more of R1, R2, R3, and R4 optionally can be bonded together to form a ring structure (preferably, a five-, six-, or seven-membered ring; more preferably, a six- or seven-membered ring). The organic and heteroorganic groups preferably have from 1 to about 20 carbon atoms (more preferably, from 1 to about 10 carbon atoms; most preferably, from 1 to about 6 carbon atoms). Preferably, R4 is not hydrogen.

Amidines comprising at least one ring structure (that is, cyclic amidines) are generally preferred. Cyclic amidines comprising two ring structures (that is, bicyclic amidines) are more preferred.

Representative examples of useful amidine compounds include 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1,4,5,6-tetrahydropyrimidine, 1-ethyl-2-isopropyl-1,4,5,6-tetrahydropyrimidine, DBU (that is, 1,8-diazabicyclo[5.4.0]-7-undecene), DBN (that is, 1,5-diazabicyclo[4.3.0]-5-nonene), and the like, and combinations thereof. Preferred amidines include 1,2-dimethyl-1,4,5,6-tetrahydropyrimidine, DBU (that is, 1,8-diazabicyclo[5.4.0]-7-undecene), DBN (that is, 1,5-diazabicyclo[4.3.0]-5-nonene), and combinations thereof, with DBU, DBN, and combinations thereof being more preferred and DBU most preferred.

Useful guanidines include those that can be represented by the following general formula:

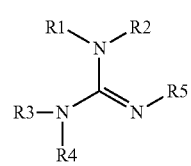

(IV)

wherein R1, R2, R3, R4, and R5 are each independently selected from hydrogen, monovalent organic groups, monovalent heteroorganic groups (for example, comprising nitrogen, oxygen, phosphorus, silicon, or sulfur in the form of groups or moieties that are preferably bonded through a carbon atom and that do not contain acid functionality such as carboxylic or sulfonic), and combinations thereof; and wherein any two or more of R1, R2, R3, R4, and R5 optionally can be bonded together to form a ring structure (preferably, a five-, six-, or seven-membered ring; more preferably, a five- or six-membered ring; most preferably, a six-membered ring). The organic and heteroorganic groups preferably have from 1 to about 20 carbon atoms (more preferably, from 1 to about 10 carbon atoms; most preferably, from 1 to about 6 carbon atoms). Preferably, R5 is not hydrogen.

Guanidines comprising at least one ring structure (that is, cyclic guanidines) are generally preferred. Cyclic guanidines comprising two ring structures (that is, bicyclic guanidines) are more preferred.

Representative examples of useful guanidine compounds include 1-methylguanidine, 1-n-butylguanidine, 1,1-dimethylguanidine, 1,1-diethylguanidine, 1,1,2-trimethylguanidine, 1,2,3-trimethylguanidine, 1,3-diphenylguanidine, 1,1,2,3,3-pentamethylguanidine, 2-ethyl-1,1,3,3-tetramethylguanidine, 1,1,3,3-tetramethyl-2-n-propylguanidine, 1,1,3,3-tetramethyl-2-isopropylguanidine, 2-n-butyl-1,1,3,3-tetramethylguanidine, 2-tert-butyl-1,1,3,3-tetramethylguanidine, 1,2,3-tricyclohexylguanidine, TBD (that is, 1,5,7-triazabicyclo[4.4.0]dec-5-ene), MTBD (that is, 7-methyl-1,5,7-triazabicyclo[4.4.0]dec-5-ene), 7-ethyl-1,5,7-triazabicyclo[4.4.0]dec-5-ene, 7-n-propyl-1,5,7-triazabicyclo[4.4.0]dec-5-ene, 7-isopropyl-1,5,7-triazabicyclo[4.4.0]dec-5-ene, 7-n-butyl-1,5,7-triazabicyclo[4.4.0]dec-5-ene, 7-isobutyl-1,5,7-triazabicyclo[4.4.0]dec-5-ene, 7-tert-butyl-1,5,7-triazabicyclo[4.4.0]dec-5-ene, 7-cyclohexyl-1,5,7-triazabicyclo[4.4.0]dec-5-ene, 7-n-octyl-1,5,7-triazabicyclo[4.4.0]dec-5-ene, 7-2-ethylhexyl-1,5,7-triazabicyclo[4.4.0]dec-5-ene, 7-decyl-1,5,7-triazabicyclo[4.4.0]dec-5-ene, biguanide, 1-methylbiguanide, 1-n-butylbiguanide, 1-(2-ethylhexyl)biguanide, 1-n-octadecylbiguanide, 1,1-dimethylbiguanide, 1,1-diethylbiguanide, 1-cyclohexylbiguanide, 1-allylbiguanide, 1-n-butyl-N2-ethylbiguanide, 1,1'-ethylenebisguanide, 1-[3-(diethylamino)propyl]biguanide, 1-[3-(dibutylamino)propyl]biguanide, N',N''-dihexyl-3,12-diimino-2,4,11,13-tetraazatetradecanediamidine, and the like, and combinations thereof. Preferred guanidines include TBD (that is, 1,5,7-triazabicyclo[4.4.0]dec-5-ene), MTBD (that is, 7-methyl-1,5,7-triazabicyclo[4.4.0]dec-5-ene), 2-tert-butyl-1,1,3,3-tetramethylguanidine, and combinations thereof. More preferred are TBD, MTBD, and combinations thereof.

If desired, the amidines and guanidines can be selected from those exhibiting a pH value lower than 13.4 when measured according to JIS Z 8802 (for example, 1,3-diphenylguanidine, DBU, DBN, or a combination thereof; preferably, DBU, DBN, or a combination thereof). The referenced method for determining the pH of aqueous solutions, JIS Z 8802, is carried out by first preparing an aqueous solution of base by adding 5 millimoles of base to 100 g of a mixed solvent composed of isopropyl alcohol and water in a weight ratio of 10:3. The pH of the resulting solution is then measured at 23° C. using a pH meter (for example, a Horiba Seisakusho Model F-22 pH meter).

Useful phosphazenes include those that can be represented by the following general formula:

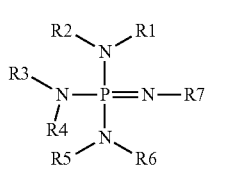

(V)

wherein R1, R2, R3, R4, R5, R6, and R7 are each independently selected from hydrogen, monovalent organic groups, monovalent heteroorganic groups (for example, comprising nitrogen, oxygen, phosphorus, silicon, or sulfur in the form of groups or moieties that are preferably bonded through a carbon atom and that do not contain acid functionality such as carboxylic or sulfonic), and combinations thereof; and wherein any two or more of R1, R2, R3, R4, R5, R6, and R7 optionally can be bonded together to form a ring structure (preferably, a five-, six-, or seven-membered ring; more preferably, a five- or six-membered ring; most preferably, a six-membered ring). The organic and heteroorganic groups preferably have from 1 to about 20 carbon atoms (more preferably, from 1 to about 10 carbon atoms; most preferably, from 1 to about 6 carbon atoms). Preferably, R7 is not hydrogen.

Representative examples of useful phosphazene compounds include

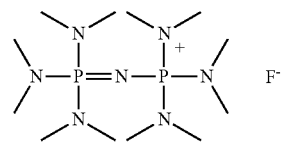

1,1,1,3,3,3-hexakis(dimethylamino)diphosphazenium fluoride

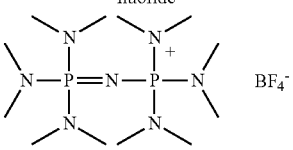

1,1,1,3,3,3-hexakis(dimethylamino)diphosphazenium tetrafluoroborate

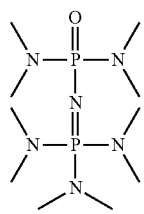

1,1,3,3,3-pentakis(dimethylamino)-1$\lambda^5$,3$\lambda^5$-diphosphazene 1-oxide

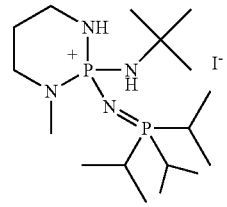

2-tert-butylamino-1-methyl-2-[tris(dimethylamino)phosphoranylidenamino]-perhydro-1,3,2-diazaphosphorinium iodide

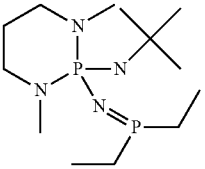

2-tert-butylimino-2-diethylamino-1,3-dimethylperhydro-1,3,2-diazaphosphorine

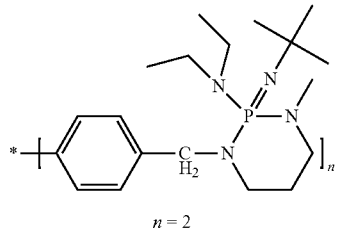

2-tert-butylimino-2-diethylamino-1,3-dimethylperhydro-1,3,2-diazaphosphorine

-continued

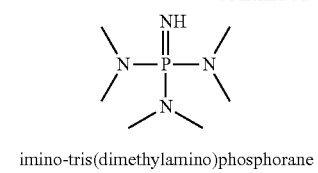
imino-tris(dimethylamino)phosphorane

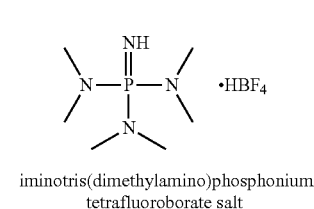
iminotris(dimethylamino)phosphonium
tetrafluoroborate salt

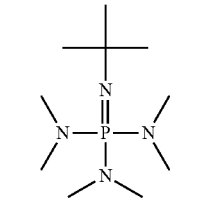
phosphazene base P$_1$-t-Bu

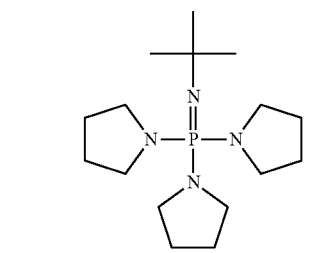
phosphazene base P$_1$-t-Bu-tris(tetramethylene)
purum

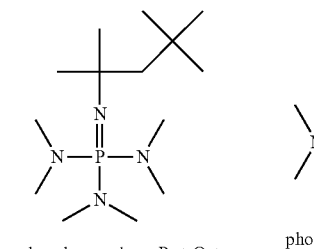
phosphazene base P$_1$-t-Oct phosphazene base P$_2$-Et purum

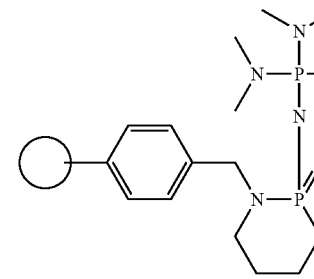
phosphazene base P$_2$-t-Bu

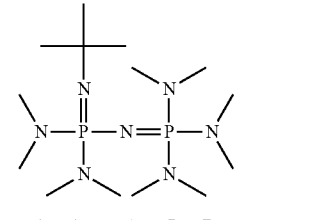
phosphazene base P$_2$-t-Bu

-continued

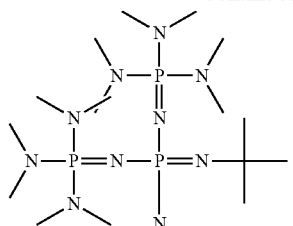
phosphazene base P$_4$-t-Bu

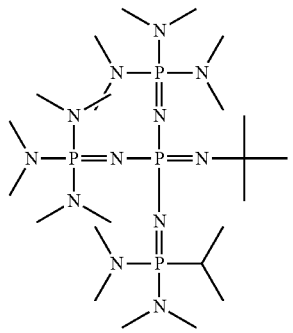
phosphazene base P$_4$-t-Bu tetrafluoroborate salt

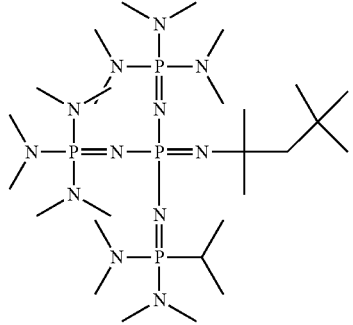
phosphazene base P$_4$-t-Oct

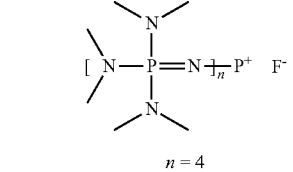

n = 4 tetrakis[tris(dimethylamino)phosphoranylidenamino] phosphonium fluoride

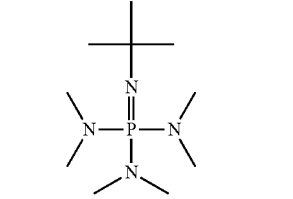
tert-butylimino-
tris(dimethylamino)phosphorane and the like, and combinations thereof. Preferred phosphazenes include 2-tert-butylimino-2-diethylamino-1,3-dimethylperhydro-1,3,2-diazaphosphorine, phosphazene base P₁-t-Bu-tris(tetramethylene), phosphazene base P₄-t-Bu, and combinations thereof.

Useful proazaphosphatrane bases (Verkade's bases) include those that can be represented by the following general formula:

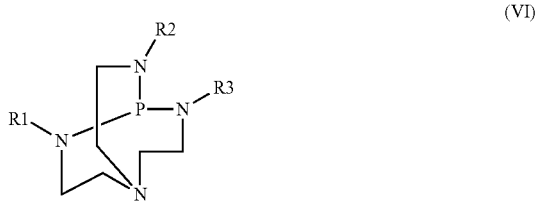

(VI)

wherein R1, R2, and R3 are each independently selected from hydrogen, monovalent organic groups, monovalent heteroorganic groups (for example, comprising nitrogen, oxygen, phosphorus, silicon, or sulfur in the form of groups or moieties that are preferably bonded through a carbon atom and that do not contain acid functionality such as carboxylic or sulfonic), and combinations thereof (less preferably hydrogen). The organic and heteroorganic groups preferably have from 1 to about 20 carbon atoms (more preferably, from 1 to about 10 carbon atoms; most preferably, from 1 to about 6 carbon atoms).

Representative examples of useful proazaphosphatrane compounds include

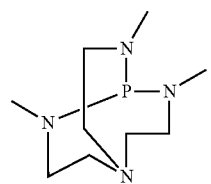

2,8,9-trimethyl-2,5,8,9-tetraaza-1-phosphabicyclo[3.3.3]undecane

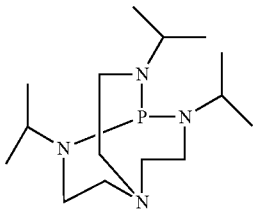

2,8,9-triisopropyl-2,5,8,9-tetraaza-1-phosphabicyclo[3.3.3]undecane

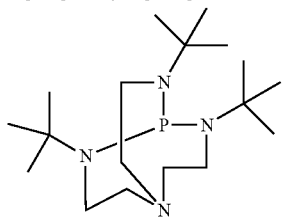

2,8,9-triisobutyl-2,5,8,9-tetraaza-1-phosphabicyclo[3.3.3]undecane and the like, and combinations thereof. 2,8,9-triisopropyl-2,5,8,9-tetraaza-1-phosphabicyclo[3.3.3]undecane is a preferred proazaphosphatrane compound.

Lewis acids suitable for use in component (c) (the catalyst composition) of the curable composition of the invention include those that can coordinate or otherwise interact with the base to form an adduct or another inhibited or latent form of the base that is at least somewhat less reactive to components (a) and/or (b) than the base itself and that can be activated (for example, by heating; preferably, under relatively mild conditions such as temperatures in the range of about 50° C. to about 120° C.) to release the base. Such Lewis acids include metal salts, triorganoborates including trialkylborates (including those represented by the formula $B(OR)_3$, wherein each R is independently alkyl) and triarylborates (including those represented by the formula $B(OR')_3$, wherein each R' is independently aryl), and the like, and combinations thereof (preferably, metal salts, trialkylborates, and combinations thereof; more preferably, metal salts and combinations thereof). If a metal-free composition is desired, however, trialkylborates and combinations thereof can be more preferred than metal salts.

Useful metal salts include those that comprise at least one metal cation that acts as a Lewis acid. Preferred metal salts include metal salts of organic acids and combinations thereof (more preferably, metal carboxylates (including both aliphatic and aromatic carboxylates; preferably, having an equivalent weight in the range of about 45 to about 425) and combinations thereof; most preferably, metal alkanoates (for example, alkanoates having up to about 18 carbon atoms; preferably, up to about 10 carbon atoms) and combinations thereof). Useful metal cations include those that have at least one vacant orbital. Preferred metals include zinc, iron, copper, bismuth, aluminum, magnesium, and combinations thereof (more preferably, zinc, bismuth, aluminum, magnesium, and combinations thereof; even more preferably, zinc, bismuth, and combinations thereof; most preferably, zinc).

Representative examples of useful metal salts include the butyrate (butanoate), octanoate, neodecanoate, and ethylhexanoate salts of the above-listed preferred metals, and the like, and combinations thereof. Preferred metal salts include the butiyrate (butanoate), octanoate, neodecanoate, and ethylhexanoate salts (most preferably, ethylhexanoate salts) of the above-listed more preferred metals, and combinations thereof. More preferred metal salts include the butiyrate (butanoate), octanoate, neodecanoate, and ethylhexanoate salts (most preferably, ethylhexanoate salts) of the above-listed even more preferred metals, and combinations thereof. Zinc (II) ethylhexanoate is particularly preferred (for example, for solubility reasons). Such metal salts can be prepared by known methods, and some (for example, zinc(II) ethylhexanoate and bismuth(III) ethylhexanoate) are commercially available.

Useful trialkylborates include those that comprise alkyl groups having from one to about five carbon atoms. Representative examples of useful trialkylborates include trimethylborate, triethylborate, triisopropylborate, tributylborate, tripentylborate, and the like, and combinations thereof. Preferred trialkylborates include trimethylborate, triethylborate, triisopropylborate, and combinations thereof (more preferably, trimethylborate, triethylborate, and combinations thereof; most preferably, trimethylborate). Such trialkylborates can be prepared by known methods, and some (for example, trimethylborate and triethylborate) are commercially available.

Useful triarylborates include those that have relatively low boiling points. Catalyst compositions comprising triarylborates can be somewhat less reactive than those comprising trialkylborates and can be used to allow higher-temperature and/or slower curing. Representative examples of useful triarylborates include triphenylborate, trinaphthylborate, tri (substituted phenyl)borates (for example, bearing one or more alkyl, alkoxy, or halogen substituents), tri(substituted naphthyl)borates (for example, bearing one or more alkyl, alkoxy, or halogen substituents), and the like, and combinations thereof. Preferred triarylborates include triphenylborate, tri(substituted phenyl)borates, and combinations thereof (more preferably, triphenylborate). Such triarylborates can be prepared by known methods, and some (for example, triphenylborate) are commercially available.

If desired, combinations of trialkylborates and triarylborates can be utilized, which combinations can be mixtures of the two and/or can include unsymmetrical borates such as alkyldiarylborates, aryldialkylborates, and combinations thereof.

The catalyst composition (component (c)) can be pre-formed or can be formed in situ by combining the Lewis acid and the base in the presence of components (a) and/or (b). If desired, the curable polysiloxane composition can optionally further comprise at least one carboxylic acid, at least one carboxylic acid anhydride, or a combination thereof (which can be included in a pre-formed catalyst composition or can be added separately in essentially any order of addition or combination of the components of the curable polysiloxane composition). Useful carboxylic acids and anhydrides include those that are relatively volatile (for example, having boiling points in the range of about 100° C. to about 150° C.). Preferably, the carboxylic acids and anhydrides are also relatively odor-free.

Representative examples of useful carboxylic acids and anhydrides include acetic acid, acetic anhydride, lactic acid, lactic anhydride, propanoic acid, propanoic anhydride, pentanoic acid, pentanoic anhydride, and the like, and combinations thereof. Preferred carboxylic acids and anhydrides include acetic acid, lactic acid, acetic anhydride, lactic anhydride, and combinations thereof (more preferably, acetic acid, acetic anhydride, and combinations thereof; most preferably, acetic acid).

Preparation of Curable Composition

The curable composition of the invention comprises components (a), (b), and (c). Preferably, the curable composition consists essentially of these three components (that is, the curable composition preferably comprises only dehydrogenatively-curable polysiloxane components).

The curable composition of the invention can be prepared by combining components (a), (b), and (c) in essentially any order (preferably, with agitation or stirring). Preferably, components (a) and (b) are combined initially, followed by addition of component (c) (preferably, as a pre-formed catalyst composition). The curable composition can be maintained as a relatively shelf-stable, 2-part system (for example, by keeping component (c) separate from the other two components), if desired, but a 1-part system (comprising all three components) can also be stable for periods of up to, for example, about several days in dry solvent (a relatively long pot life), prior to coating or other application of the composition.

The relative amounts of components (a) and (b) can vary widely, depending upon their nature and the desired properties of the curable and/or cured composition. Although stoichiometry prescribes a 1:1 molar ratio of reactive silane functionality (for example, one mole of hydrosilyl moieties for every mole of hydroxysilyl moieties), in practice it can be useful to have a deficiency or an excess of hydrosilyl functionality (for example, this can be useful when cure inhibitors are present). Molar ratios (of hydrosilyl moieties to hydroxysilyl moieties) up to, for example, about 8:1 or about 13:1 or even as high as about 35:1 can be useful. Component (c) (the catalyst composition) can be present in the curable composition in amounts ranging from about 0.1 to about 10 weight percent (preferably, from about 0.1 to about 5 weight percent; more preferably, from about 0.5 to about 2 weight percent), based upon the total weight of components (a), (b), and (c). The base and the Lewis acid can generally be used in stoichiometric molar amounts (based upon the number of vacant orbitals of the Lewis acid that are available to receive an electron pair from the base). When zinc (II) salt(s) (having at least two such vacant orbitals) are used as the Lewis acid(s), however, a sub-stoichiometric molar ratio of 1:1 (base:Lewis acid) can be preferred over a stoichiometric ratio of 2:1. For example, somewhat better catalytic performance (in the form of a more controlled, slower reaction and longer bath life at room temperature, as well as better cure upon heating) can be provided by the former ratio at relatively low cure temperatures.

If desired, the catalyst composition can optionally further contain at least one carboxylic acid or anhydride in amounts ranging from about 1 to about 50 weight percent (preferably, from about 10 to about 40 weight percent; more preferably, from about 20 to about 30 weight percent), based upon the total weight of the base and the carboxylic acid or anhydride. Alternatively (and preferably), the optional carboxylic acid or anhydride can be separately added to the curable composition in such amounts.

Preferably, the curable composition comprises at least one solvent or diluent (preferably, a substantially dry solvent or diluent) to aid in storage stability, mixing, and/or coating, particularly when components (a) and (b) are polymeric. Suitable solvents for use in the curable composition of the invention include aprotic solvents such as aromatic solvents (for example, xylene, toluene, 1,2-dichlorobenzene, 1,3-dichlorobenzene, 1,4-dichlorobenzene, and the like, and mixtures thereof), ketones (for example, methyl ethyl ketone (MEK), cyclohexanone, and the like, and mixtures thereof), alkyl esters (for example, ethyl acetate, butyl acetate, and the like, and mixtures thereof), alkanes (for example, heptane, isoparaffinic hydrocarbons, and the like, and mixtures thereof), ethers (for example, t-butyl methyl ether, tetrahydrofuran (THF), and the like, and mixtures thereof), and the like, and mixtures thereof. Preferred solvents include aromatic solvents, alkanes, ketones, and mixtures thereof; with xylene, heptane, methyl ethyl ketone, and mixtures thereof being more preferred and heptane, methyl ethyl ketone, and mixtures thereof most preferred.

Minor amounts of optional components can be added to the curable composition to impart particular desired properties for particular curing methods or uses. Useful compositions can comprise conventional additives such as, for example, catalysts (including conventional condensation catalysts such as tin catalysts, which can be added as co-catalysts if desired), initiators, emulsifiers (including surfactants), stabilizers, anti-oxidants, flame retardants, adhesion promoters (for example, trialkoxysilanes), release modifiers (for example, silicate MQ resin), colorants, thickeners (for example, carboxy methyl cellulose (CMC), polyvinylacrylamide, polypropylene oxide, polyethylene oxide/polypropylene oxide copolymers, polyalkenols), water scavengers, and the like, and mixtures thereof.

If desired, the curable composition can be prepared in the form of an emulsion (for example, by using water as a diluent), although such a form can be less preferred (for example, due to the potential occurrence of competing side reactions in the presence of water). Useful emulsifiers (also known as emulgents) include surface active substances or surfactants. Silicone emulsions often contain water, silicone oil, stabilizing surfactants, preservatives, and other additives for viscosity stabilization and freeze-thaw stability.

The curable composition of the invention can be prepared in the form of an emulsion by any of a variety of known or hereafter-developed mechanical or chemical emulsification techniques. Some suitable emulsions are also commercially available (for example, Syl-Off™ 1181 aqueous emulsion coating composition, available from Dow Corning Corporation, Midland, Mich.) and can be used in combination with the catalyst composition (component (c)). Useful emulsification techniques include those described, for example, in European Patent Applications Nos. 0 268 982 (Toray Silicone Company, Ltd.), 0 459 500 (Dow Corning Corporation), and 0 698 633 (Dow Corning Corporation), the descriptions of the techniques being incorporated herein by reference.

A particularly useful technique for producing silicone in water emulsions is that described in U.S. Pat. No. 6,013,682 (Dalle et al.), the technique description being incorporated herein by reference. This technique provides emulsions in which silicones polymerize by chain extension at the interior of silicone droplets suspended in water. U.S. Pat. No. 5,229,212 (Reed) describes another useful technique in which a high molecular weight, water-soluble or water-dispersible polymeric thickening agent (such as polyethylene oxide) is utilized, the description of the technique being incorporated herein by reference.

Suitable emulsifiers for use in the curable composition of the invention include non-ionic (including polymeric non-ionic surfactants (for example, alkylpolysaccharide)), cationic, anionic, and amphoteric surfactants, and the like, and combinations thereof. The surfactants can be used individually or in combination. Although essentially any type of surfactant can be used, non-ionic surfactants can be preferred.

Useful non-ionic surfactants include those that are rendered hydrophilic by the presence of a polyethylene glycol chain (obtained by the polycondensation of ethylene oxide). Such non-ionic surfactants are termed "polyethoxylated non-ionics." Other examples of useful non-ionic surfactants include polyalkenols (also known as polyvinyl alcohols), polyoxyalkylene alkyl ethers, polyoxyalkylene sorbitan alkyl esters, polyoxyalkylene alkyl esters, polyoxyalkylene alkylphenol ethers, polyethylene glycols, polypropylene glycols, diethylene glycols, polyethylene oxide-polypropylene oxide block copolymers, ethoxylated or sulfonated resins, carboxymethyl cellulose and other polysaccharide derivatives, polyacrylates, xanthane, and the like, and combinations thereof. Preferred non-ionic surfactants include polymeric non-ionic surfactants and combinations thereof (more preferably, polyalkenols and combinations thereof).

Examples of useful cationic surfactants include quaternary ammonium hydroxides (for example, tetramethylammonium hydroxide, octyltrimethylammonium hydroxide, dodecyltrimethylammonium hydroxide, hexadecyltrimethylammonium hydroxide, octyldimethylbenzylammonium hydroxide, decyldimethylbenzyl ammonium hydroxide, didodecyldimethylbenzyl ammonium hydroxide, dioctadecyldimethylammonium hydroxide, tallow trimethylammonium hydroxide, cocotrimethylammonium hydroxide, and the like, and combinations thereof), corresponding salts of the quaternary ammonium hydroxides, fatty acid amines and amides and their derivatives, salts of the fatty acid amines and amides (including aliphatic fatty amines and amides) and their derivatives, homologs of aromatic amines having fatty chains, fatty amides derived from aliphatic diamines, fatty amides derived from disubstituted amines, derivatives of ethylene diamine, amide derivatives of amino alcohols, amine salts of long-chain fatty acids, quaternary ammonium bases derived from fatty amides of disubstituted diamines, quaternary ammonium bases of benzimidazolines, basic compounds of pyridinium and its derivatives, sulfonium compounds, quaternary ammonium compounds of betaine, urethanes of ethylene diamine, polyethylene diamines, polypropanolpolyethanol amines, and the like, and combinations thereof.

Examples of useful anionic surfactants include alkylbenzene sulfonates (detergents), fatty acids (soaps), alkyl sulfates such as lauryl sulfate (foaming agents), di-alkyl sulfosuccinates (wetting agents), lignosulfonates (dispersants), and the like, and combinations thereof. Other useful anionic surfactants include those described in U.S. Pat. No. 6,013,682 (Dalle et al.), the descriptions thereof being incorporated herein by reference.

Another class of useful surfactants is that of amphoteric or zwitterionic surfactants, which include single surfactant molecules that exhibit both anionic and cationic dissociations. Examples of useful amphoteric surfactants include betaines, sulfobetaines, natural substances such as aminoacids and phospholipids, and the like, and combinations thereof.

The amount of surfactant that can be included in the curable composition of the invention will vary (for example, depending upon the nature of the surfactant(s)). Amounts of surfactant in the range of about 0.01 to about 35 weight percent (based upon the total weight of the curable composition), however, can often be useful (with amounts in the range of about 0.1 to about 20 weight percent being preferred, and amounts in the range of about 0.5 to about 5 or 10 weight percent being more preferred). The total amount of water that can be included in the curable composition to form an aqueous emulsion can also vary but generally can be in the range of about 20 to about 95 weight percent (based upon the total weight of the curable composition).

If desired, the catalyst composition (component (c)) can be pre-emulsified (for example, by addition of the catalyst composition to an aqueous solution of surfactant and/or thickening agent, followed by shaking or agitation of the resulting mixture) prior to its combination with the other components of the curable composition.

Use and Curing of Curable Composition

The curable composition of the invention can be used in various different applications. For example, the composition(s) can be used as sealants, release coatings, surface treatments, hardcoats, and the like. When used as fluorinated surface treatments, a degree of hydrophobicity and/or oleophobicity can be imparted to a variety of substrates (for example, for surface protection or to enhance ease of cleaning).

The curable composition of the invention (or, alternatively, its components) can be applied to at least a portion of at least one major surface of a substrate (for example, a sheet, a fiber, or a shaped object) by essentially any known or hereafter-developed application method, so as to form a variety of different coated articles. The composition can be applied in essentially any manner (and with essentially any thickness) that can form a useful coating.

Useful application methods include coating methods such as dip coating, spin coating, spray coating, wiping, roll coating, wire coating, and the like, and combinations thereof. The composition can be applied in neat form or in the form of solvent solutions (for example, in solvents such as alkyl esters, ketones, alkanes, aromatics, and the like, and mixtures thereof) or emulsions. When solvent is used, useful concentrations of the composition can vary over a wide range (for example, from about 1 to about 90 weight percent), depending upon the viscosity of the composition, the application method utilized, the nature of the substrate, and the desired properties.

Substrates suitable for use in preparing the coated articles include those having at least one surface comprising a material that is solid and preferably substantially inert to any coating or application solvent that is used. Preferably, the curable composition can adhere to the substrate surface through chemical interactions, physical interactions, or a combination thereof (more preferably, a combination thereof).

Suitable substrates can comprise a single material or a combination of different materials and can be homogeneous or heterogeneous in nature. Useful heterogeneous substrates include coated substrates comprising a coating of a material (for example, a metal or a primer) borne on a physical support (for example, a polymeric film).

Useful substrates include those that comprise wood, glass, minerals (for example, both man-made ceramics such as concrete and naturally-occurring stones such as marble and the like), polymers (for example, polycarbonate, polyester, polyacrylate, and the like) including multi-layer polymeric films, metals (for example, copper, silver, gold, aluminum, iron, stainless steel, nickel, zinc, and the like), metal alloys, metal compounds (for example, metal oxides and the like), leather, parchment, paper, textiles, painted surfaces, and combinations thereof. Preferred substrates include glass, minerals, wood, paper, metals, metal alloys, metal compounds, polymers, and combinations thereof (more preferably, paper, metals, metal alloys, metal compounds, polymers, and combinations thereof).

Preferred substrates include those used for pressure-sensitive adhesive (PSA) products. For example, the curable composition can be applied to suitable flexible or inflexible backing materials and then cured. Useful flexible backing materials include paper, Kraft paper, polyolefin-coated paper, plastic films (for example, poly(propylene), poly(ethylene), poly(vinyl chloride), polyester (including poly(ethylene terephthalate), polyamide, cellulose acetate, and ethyl cellulose), and the like, and combinations thereof, although essentially any surface requiring release toward adhesives can be utilized. Backings can thus also be of woven fabric formed of threads of synthetic or natural materials such as cotton, nylon, rayon, glass, or ceramic material, or they can be of nonwoven fabric such as air-laid webs of natural or synthetic fibers or blends of these. In addition, suitable backings can be formed of metal, metallized polymeric film, or ceramic sheet material. Primers (including surface treatments such as corona treatment) can be utilized, but they are not always necessary.

The curable composition of the invention can provide coatings that are suitable for use in the manufacture of PSA-coated labels and tapes. The specific level of release provided upon curing can be controllably varied through variation in, for example, the weight percentage and molecular weight of component (a) of the composition, or through the addition of release modifiers (for example, silicate MQ resin), which also can be varied in nature and/or amount.

The curable composition can be cured by concentration (for example, by allowing solvent evaporation). The preferred curing conditions will vary, depending upon the particular application and its accompanying requirements and conditions. Moisture can be present but generally is not necessary. Cure generally can be effected at temperatures ranging from room temperature (for example, about 20-23° C.) up to about 150° C. or more (preferably, temperatures of about 20° C. to about 125° C.; more preferably, about 40° C. to about 120° C.; most preferably, about 60° C. to about 110° C.). Curing times can range from a few seconds (for example, at about 110° C.) to hours (for example, under low catalyst or somewhat lower temperature conditions) to days (for example, at room temperature).

Release coatings obtained via cure of the curable composition of the invention generally contain little or no free silicone to adversely affect the tack and peel properties of PSAs that come in contact with them. The curable composition of the invention can cure relatively rapidly to provide relatively firmly anchored, highly crosslinked, solvent-resistant, tack-free coatings, which can be used with a broad range of PSA types (for example, acrylates, tackified natural rubbers, and tackified synthetic elastomers).

Articles in the form of PSA laminates (for example, comprising a layer of PSA borne on a release liner) can be prepared by placing a PSA layer in contact with the release coating through dry lamination, wet solution casting, or even by application of a photopolymerizable composition to the release coating, followed by irradiation to effect photopolymerization (for example, as described in U.S. Pat. No. 4,181,752 (Martens et al.), the description of which is incorporated herein by reference). Such articles can exhibit relatively good storage stability (as evidenced, for example, by the results of room temperature and/or heat accelerated aging tests to evaluate any change in the level of release (peel force) from the release coating and/or in the subsequent level of adhesion to a desired substrate).

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals were obtained from, or are available from, chemical suppliers such as Aldrich Chemical Company, Milwaukee, Wis.

| Material | Description | Source |
| --- | --- | --- |
| SYL-OFF ™ 7048 | Hydrosilyl-functional polysiloxane crosslinker, trade designation "SYL-OFF ™ 7048 CROSSLINKER." | Dow Corning Corporation, Midland, MI. |
| SYL-OFF ™ 2792 | A 32 weight percent solids dispersion of a blend of reactive silanol terminated siloxane polymers in toluene, trade designation "SYL-OFF ™ 2792." | Dow Corning Corporation, Midland, MI. |

| Material | Description | Source |
|---|---|---|
| SYL-OFF ™ 292 | A 30 weight percent solids dispersion of a blend of reactive hydroxysilyl-functional siloxane polymer(s) (said to comprise hydroxyl-terminated polydimethylsiloxane) and hydrosilyl-functional polysiloxane crosslinker (said to comprise poly(methyl)(hydrogen)siloxane) in xylene. This product is designed to provide premium release in most applications and is sold under the trade designation "Syl-Off ™ 292." | Dow Corning Corporation, Midland, MI. |
| Zinc Bis(2-ethylhexanoate) | $Zn(OOCCH(CH_2CH_3)CH_2CH_2CH_2CH_3)_2$, 80 weight percent in mineral spirits. | Alfa-Aesar, Ward Hill, MA. |
| Bismuth Tris(2-ethylhexanoate) | $Bi(OOCCH(CH_2CH_3)CH_2CH_2CH_2CH_3)_3$, 92 weight percent in 2-ethylhexanoic acid. | Alfa-Aesar, Ward Hill, MA. |
| DBU | 1,8-Diazabicyclo(5.4.0)undec-7-ene. | TCI America, Portland, OR. |
| TBD | 1,5,7-Triazabicyclo[4.4.0]dec-5-ene. | Sigma-Aldrich Chemical Company, St. Louis. MO. |
| Triethylborate | | Sigma-Aldrich Chemical Company, St. Louis. MO. |
| Trimethylborate | | Sigma-Aldrich Chemical Company, St. Louis. MO. |
| MEK | Methyl Ethyl Ketone | EMD Chemicals, Gibbstown, NJ. |
| MIBK | Methyl Isobutyl Ketone | |
| Deuterated Pyridine | | Sigma-Aldrich Chemical Company, St. Louis. MO. |

Preliminary Screening of Bases 1-10 and Comparative Bases C-1-C-12

A sample of a 30 weight percent solids dispersion of a blend of reactive hydroxysilyl-functional siloxane polymer(s) (said to comprise hydroxyl-terminated polydimethylsiloxane) and hydrosilyl-functional polysiloxane crosslinker (said to comprise poly(methyl)(hydrogen)siloxane) in xylene (a premium release coating composition obtained from Dow Corning Corporation, Midland, Mich., under the trade designation Syl-Off™ 292) was diluted to 10 weight percent solids with heptane. For each of Bases 1-10 and Comparative Bases C-1-C-12, 0.02 g of base (listed in Table 1 below; all bases were obtained from Aldrich Chemical Company, Milwaukee, Wis.) was added to 5 g of Syl-Off™ 292 solution (10 weight percent in heptane) and then mixed. The resulting mixtures were coated on the primed side of a 50 micrometer thick polyester terephthalate (PET) film (obtained from Mitsubishi Polyester Film, Greer, S.C., under the trade designation Hostaphan™ 3SAB, referred to hereinafter as 3SAB PET film, which has one side chemically treated or primed to improve the adhesion of silicone coatings) using a number 4 Meyer rod. The resulting coated 3SAB PET samples were set aside at room temperature (about 23° C.) and their curing status (level of tackiness) was monitored. A coated sample was deemed cured if the coating solidified within 5 minutes. A coated sample was deemed not cured if the coating did not solidify and remained tacky for at least 24 hours at room temperature. The results of the base screening are shown in Table 1 below.

TABLE 1

| Base No. | Base | Curing |
|---|---|---|
| 1 | DBU (1,8-Diazabicyclo[5.4.0]undec-7-ene) 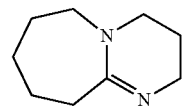 | Yes |
| 2 | DBN (1,5-Diazabicyclo[4.3.0]non-5-ene) 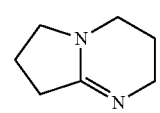 | Yes |
| 3 | 1,2-Dimethyl-1,4,5,6-tetrahydropyrimidine 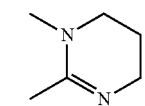 | Yes |
| 4 | TBD (1,5,7-Triazabicyclo[4.4.0]dec-5-ene) 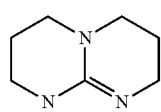 | Yes |

TABLE 1-continued

| Base No. | Base | Curing |
|---|---|---|
| 5 | MTBC (7-Methyl-1,5,7-triazabicyclo[4.4.0]dec-5-ene) 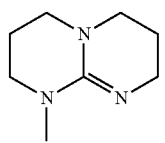 | Yes |
| 6 | 2-tert-Butyl-1,1,3,3-tetramethylguanidine 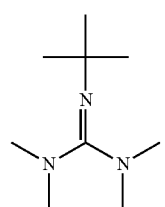 | Yes |
| 7 | Phosphazene base P$_1$-t-Bu-tris(tetramethylene) 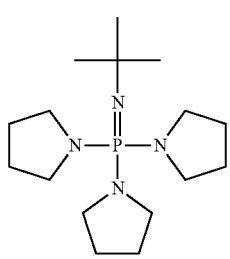 | Yes |
| 8 | Phosphazene base P$_4$-t-Bu solution (1M in Hexane) 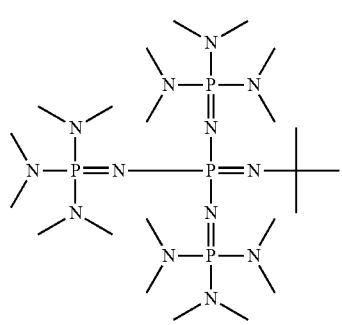 | Yes |
| 9 | 2-tert-Butylimino-2-diethylamino-1,3-dimethylperhydro-1,3,2-diazaphosphorine 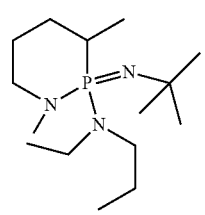 | Yes |
| 10 | 2,8,9-Triisopropyl-2,5,8,9-tetraaza-1-phosphabicyclo[3,3,3]undecane 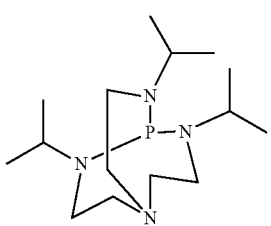 | Yes |
| C-1 | 1,1,3,3-Tetramethylguanidine 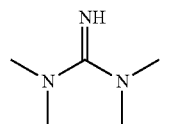 | No |
| C-2 | N,N′-Diisopropylcarbodiimide 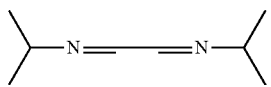 | No |
| C-3 | N,N′-Dicyclohexylcarbodiimide 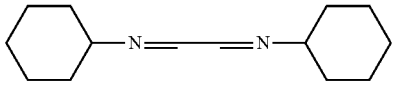 | No |
| C-4 | Imidazole 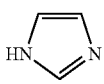 | No |
| C-5 | N-Methylimidazole 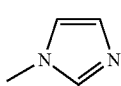 | No |
| C-6 | 1,2-Dimethylimidazole 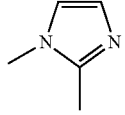 | No |
| C-7 | 1,4-Diazabicyclo[2.2.2]octane 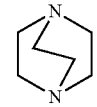 | No |
| C-8 | 4,4′-Trimethylenebis(1-methylpiperidine) 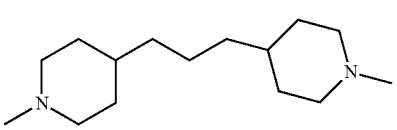 | No |

TABLE 1-continued

| Base No. | Base | Curing |
|---|---|---|
| C-9 | 2,6-Dimethylpyridine | No |
| C-10 | 4-Dimethylaminopyridine | No |
| C-11 | 2,2,6,6-Tetramethylpiperidine | No |
| C-12 | | No |

Method for Testing Release Liner Adhesion (Release Test)

This test measured the effectiveness of release liners (prepared using the compositions of the Examples and Comparative Examples described below) that had been aged for a period of time at a constant temperature and relative humidity. The aged release value is a quantitative measure of the force required to remove a flexible adhesive from the release liner at a specific angle and rate of removal.

The 180° angle peel adhesion strength of a release liner to an adhesive sample was measured in the following manner, which is generally in accordance with the test method described in Pressure Sensitive Tape Council PSTC-101 Method D (Rev 05/07) "Peel Adhesion of Pressure Sensitive Tape."

The Example and Comparative Example release liners prepared as described below were coated with an acrylic radiation-sensitive syrup of liquid monomers (a mixture of 90 parts by weight isooctyl acrylate and 10 parts by weight acrylic acid; less than 10 percent polymerized; essentially as described in Examples 1-7 of U.S. Pat. No. 4,181,752 (Martens et al.), the description of which is incorporated herein by reference) with a notched bar coater to form a continuous web of acrylic syrup nominally 50 micrometers thick. The resulting coated web was then polymerized to more than 95 percent conversion by exposing the acrylic syrup to ultraviolet-A (UV-A) radiation in a nitrogen inert environment. The UV source was a 20 W 350 BL lamp (available from Osram Sylvania, Danvers, Mass.). Upon curing, the polymerized syrup formed a pressure-sensitive adhesive (PSA) transfer tape on the release liner. The resulting adhesive transfer tape-release liner construction was aged for 7 days or as described below prior to testing (for release liner adhesion and liner-side stainless steel (SS) peel adhesion).

After aging, a sample of the adhesive transfer tape-release liner construction was cut 2.54 cm wide and approximately 20 cm in length using a specimen razor cutter. The sample was applied with its exposed adhesive side down and lengthwise onto the platen surface of a peel adhesion tester (IMASS Slip/Peel Tester, Model 3M90, obtained from Instrumentors, Incorporated, Strongsville, Ohio). The applied sample was rubbed down on the test panel using light thumb pressure. The sample on the platen surface was rolled twice with a 2 kg rubber roller at a rate of 61 cm per minute.

The release liner portion of the sample was carefully lifted away from the adhesive transfer tape portion of the sample on the platen surface, was doubled back at an angle of 180°, and was secured to the clamp of the peel adhesion tester. The 180° angle release liner peel adhesion strength was then measured at a peel rate of 38.1 mm per second. A minimum of three test samples were evaluated with results obtained in grams-force per inch (g/inch), which results were used to calculate the average peel force. This average peel force was then converted to Newtons per decimeter (N/dm). All release tests were carried out in a facility at constant temperature (23° C.) and constant relative humidity (50 percent).

Method for Testing Liner-Side Stainless Steel (SS) Peel Adhesion (Readhesion Test)

Measurements were taken to determine whether a drop in adhesion value occurred due to undesirable contamination of the adhesive surface by the release coating of the release liner. These measurements were also carried out at 23° C. and 50 percent relative humidity. At least two measurements were made for each Example and Comparative Example, and the resulting data are reported as an average of all measurements. Measurements were made in g/inch and converted to N/dm.

The 90° angle peel adhesion strength of a tape sample to stainless steel (SS) was measured using the procedure described below, which is generally in accordance with the test method described in Pressure Sensitive Tape Council PSTC-101 Method C (Rev 05/07) "Peel Adhesion of Pressure Sensitive Tape." The test was run at 23° C. (73.4° F.) and 50 percent relative humidity (RH).

A 50 micrometer thick PET film (obtained from Mitsubishi Polyester Film, Greer, S.C. under the trade designation "3SAB PET") was laminated to the adhesive side of adhesive transfer tape-release liner constructions prepared essentially as described above. A sample of each construction was then cut 1.27 cm wide and approximately 20 cm in length using a specimen razor cutter. The release liner portion of the sample was carefully removed to expose the adhesive that was against the release liner surface. The resulting sample was applied with its exposed adhesive side down and lengthwise onto the surface of a stainless steel (SS) test panel measuring 12.5 cm long by 5 cm wide, the sample extending beyond the length of one end of the panel. The applied sample was rubbed down on the test panel using light thumb pressure. The test panel with the applied sample (adhesive-backed PET film) was rolled twice with a 2 kg rubber roller at a rate of 61 cm per minute.

Each sample was then equilibrated for 15 minutes at 23° C. and 50 percent RH. After equilibration, the sample was placed in a 90° angle test fixture on a peel adhesion tester (IMASS Slip/Peel Tester, Model 3M90, obtained from Instrumentors, Incorporated, Strongsville, Ohio). An extended end of the sample was secured in the clamps of the peel adhesion tester, and peel adhesion was measured at a peel rate of 30.5 cm per minute. A minimum of two test samples were evaluated with results obtained in ounces-force per 0.5 inch, which results were used to calculate the average peel force. This average peel force was then converted to Newtons per decimeter (N/dm).

Silicone Coating Weight Determination

Coating weights were determined by punching samples (about 3.69 cm in diameter) of coated and uncoated substrates and then comparing the weight differences between the resulting coated and uncoated samples using an energy-dispersive X-ray fluorescence (EDXRF) spectrophotometer (obtained from Oxford Instruments, Elk Grove Village, Ill. under the trade designation OXFORD LAB X3000).

Percent Extractable Silicone Determination

The percentage of extractable silicone (that is, unreacted silicone), a measure of the extent of silicone cure on a release liner, was measured by the following method within 15 minutes after coating (of curable silicone compositions, as described in the Examples and Comparative Examples below) and again after 7 days.

Extractables were measured on cured thin film formulations to ascertain the extent of silicone crosslinking. The initial coating weight of a 2.54 cm diameter sample of coated substrate was determined according to the Silicone Coating Weight Determination procedure described above. The coated sample was then dipped and shaken in methyl isobutyl ketone (MIBK) for 5 minutes, was removed, and was allowed to dry. The coating weight of the removed sample was then measured again (to obtain a final coating weight), and the resulting difference between the initial and final coating weights was recorded as the percentage of extractable silicone.

Percent Extractable Silicone was calculated using the following formula:

$$[(a-b)/a] \times 100 = \text{Percent Extractable Silicone}$$

where a=initial coating weight (before extraction with MIBK)

where b=final coating weight (after extraction with MIBK)

$^{13}$C and $^{1}$H-$^{15}$N Nuclear Magnetic Resonance (NMR) Analysis

The sample was dissolved in deuterated pyridine. $^{13}$C NMR spectra were acquired on a Bruker AVANCE™ 500 MHz NMR spectrometer obtained from Bruker AXS Inc., Madison, Wis. $^{1}$H-$^{15}$N Heteronuclear Multiple-Bond Correlation (HMBC) NMR spectra were acquired on a Varian INOVA™ 500 MHz spectrometer obtained from Agilent Technologies, Inc., Santa Clara, Calif.

Preparation of Catalyst Composition Number (No.) 1 (Comprising DBU and Zinc Bis(2-ethylhexanoate) (1:1))

DBU (15.2 g, 0.1 mol) was mixed with 43.9 g zinc bis(2-ethylhexanoate) (80 weight percent in mineral spirits, 0.1 mol) and left overnight. The formation of a zinc bis(2-ethylhexanoate):DBU (1:1) adduct was supported by $^{13}$C and $^{1}$H-$^{15}$N nuclear magnetic resonance (NMR) analysis. For example, the $^{15}$N chemical shifts of the single- and double-bonded nitrogen atoms (labeled N-1 and N-5 respectively) of DBU were as follows:

| Sample | N-1 | N-5 |
|---|---|---|
| DBU | 87.8 | 209.1 |
| DBU-Zn Ethylhexanoate | 103.6 | 161.1 |
| DBU-Zn Acetate | 112.2 | 133 |

Preparation of Catalyst Composition No. 2 (Comprising DBU and Zinc Bis(2-ethylhexanoate) (2:1))

DBU (30.4 g, 0.2 mol) was mixed with 43.9 g zinc bis(2-ethylhexanoate) (80 weight percent in mineral spirits, 0.1 mol) and left overnight.

Preparation of Catalyst Composition No. 3 (Comprising TBD and Zinc Bis(2-ethylhexanoate) (1:1))

TBD (13.9 g, 0.1 mol) was mixed with 43.9 g zinc bis(2-ethylhexanoate) (80 weight percent in mineral spirits, 0.1 mol) and left overnight.

Preparation of Catalyst Composition No. 4 (Comprising DBU and Bismuth Tris(2-ethylhexanoate) (1:1))

DBU (1.52 g, 0.01 mol) was mixed with 6.93 g (0.01 mol) of 92 weight percent bismuth tris(2-ethylhexanoate) and left overnight.

Preparation of Catalyst Composition No. 5 (Comprising DBU and Triethylborate (1:1))

DBU (15.2 g, 0.1 mol) was mixed with 14.5 g (0.1 mol) triethylborate and left overnight.

Preparation of Catalyst Composition No. 6 (Comprising DBU and Trimethylborate (1:1))

DBU (15.2 g, 0.1 mol) was mixed with 10.3 g (0.1 mol) trimethylborate and left overnight.

Preparation of Catalyst Composition No. 7 (Comprising TBD and Triethylborate (1:1))

TBD (13.9 g, 0.1 mol) was mixed with 14.5 g (0.1 mol) triethylborate and left overnight.

Comparative Example A

Heptane (12.0 g), toluene (12.0 g), SYL-OFF™ 7048 (0.44 g), SYL-OFF™ 2792 (14.66 g), and zinc bis(2-ethylhexanoate) (0.3 g, as the sole component of a catalyst composition) were thoroughly mixed and coated on the glossy side of a 58#, corona-treated, polyethylene-coated kraft paper (PCK, obtained from Jen-Coat, Inc., Westfield, Mass.) with a #4 Meyer bar. The resulting coating was cured at 80° C. for 2 minutes in an oven equipped with solvent exhaust. The coating was then tested by rubbing with a thumb, resulting in a greasy smear. The coating was tested with a thumb again after two more hours of curing at 80° C. and still produced a greasy smear.

Examples 1-7 and Comparative Example B

Curable formulations were prepared in the same manner as Comparative Example A above, except that the catalyst composition was varied as described in Table 2 below. The curable formulations of each of Examples 1-7 and Comparative Example B were thoroughly mixed and observed for outgassing. Then each formulation was coated on the glossy side of a 58#, corona-treated, polyethylene-coated kraft paper (PCK, obtained from Jen-Coat, Inc., Westfield, Mass.) with a #4 Meyer bar. The resulting coatings were cured at various temperatures (shown in Table 2) for 2 minutes in an oven equipped with solvent exhaust. The degree of cure achieved and attachment to the paper substrate were then evaluated by rubbing the cured coatings with a thumb. A "smear" indicated little or no cure; "rub off" indicated cure but poor anchorage; and "good" indicated cure and anchorage. Table 2 below summarizes the cure behavior of the formulations of Examples 1-7 and Comparative Examples A and B at various temperatures.

TABLE 2

| Example No. | Catalyst Composition | Outgas (Yes/No) | Bath Life (Hours)* | Rub Test after Cure @ Temperature (° C.) | | | |
|---|---|---|---|---|---|---|---|
| | | | | 23 | 50 | 80 | 100 |
| 1 | No. 1 | No | 4 | Smear | | Good | Good |
| 2 | No. 2 | | | | | | |
| 3 | No. 3 | No | >4 | Smear | Slight Smear | | Good |
| 4 | No. 4 | No | <1 | Smear | | Good | |
| 5 | No. 5 | No | >24 | Good | Good | | |
| 6 | No. 6 | No | >24 | Good | Good | | |

TABLE 2-continued

| Example No. | Catalyst Composition | Outgas (Yes/No) | Bath Life (Hours)* | Rub Test after Cure @ Temperature (° C.) | | | |
|---|---|---|---|---|---|---|---|
| | | | | 23 | 50 | 80 | 100 |
| 7 | No. 7 | Yes | | Good | Good | | |
| C-A | Zinc Bis(2-ethyl-hexanoate) | No | >4 | Smear | | Smear | |
| C-B | DBU | Yes | <1 | Good | Good | Smear | Smear |

*where ">" means greater than, and "<" means less than

Example 8

The curable formulation of Example 1 (25 weight percent solids) was prepared essentially as described above. To samples of the formulation varying amounts (0, 0.1, 0.2, 0.4, and 0.8 weight percents, respectively) of acetic acid were added, and the viscosity of each resulting sample was monitored using a Brookfield viscometer (Model DV-II+, obtained from Brookfield Engineering Laboratories, Inc., Middleboro, Mass.). Table 3 below summarizes the bath lives (in minutes) observed for the samples versus their acetic acid content (weight percent, based upon the total weight of curable formulation and acetic acid). Bath life was taken to be the time at which the viscosity of the sample started increasing very rapidly.

TABLE 3

| Acetic Acid Content (weight percent) | Bath Life (minutes) |
|---|---|
| 0.00 | 60 |
| 0.10 | 50 |
| 0.20 | 100 |
| 0.40 | 210 |
| 0.80 | 460 |

Examples 9-11 and Comparative Example C

Curable formulations were prepared by combining all ingredients and thoroughly mixing them for each Example and Comparative Example. Table 4 below summarizes the ingredients used, their amounts (in grams), and the compositions of the resulting formulations. Catalyst Composition No. 1 was used for Examples 9-11, and DBU alone was used as the catalyst composition for Comparative Example C. The solvents were dried before use (with calcium sulfate) to a water content of about 45 ppm.

TABLE 4

| | Curable Formulation | | | | | | | |
|---|---|---|---|---|---|---|---|---|
| | Solvent | | | | | Stabilizer | | |
| Example No. | Heptane (g) | Toluene (g) | SYL-OFF ™ 2792 (g) | SYL-OFF ™ 7048 (g) | Catalyst Composition (g) | Acetic Anhydride (g) | Acetic Acid (g) | Percent Solids |
| 9 | 7.52 | 7.52 | 9.16 | 0.27 | 0.26 | | | 13.11 |
| 10 | 7.57 | 7.57 | 9.02 | 0.27 | 0.25 | 0.05 | | 13.12 |
| 11 | 7.57 | 7.57 | 9.02 | 0.27 | 0.25 | | 0.05 | 13.12 |
| C-C | 7.52 | 7.52 | 9.16 | 0.27 | 0.07 | | | 13.11 |

The curable formulations of Examples 9-11 and Comparative Example C were aged for 1 hour and were then coated on the glossy side of a 58#, corona-treated, polyethylene-coated kraft paper with a #4 Meyer bar. The resulting coatings were cured at 80° C. for 2 minutes in an oven equipped with solvent exhaust. The resulting cured coatings were then tested to determine their silicone coating weights, percent extractable silicones, release liner adhesion, and liner-side peel adhesion (readhesion) using the methods described above. Table 5 below summarizes the test data for Examples 9-12 and Comparative Example C.

TABLE 5

| Example No. | Silicone Coating Weight (g) | Percent Extractable Silicone | Release Liner Adhesion (N/dm) | Readhesion (N/dm) |
|---|---|---|---|---|
| 9 | 0.53 | 17.1 | 0.98 | 27.14 |
| 10 | 0.60 | 8.0 | 0.92 | 31.08 |
| 11 | 0.76 | 5.1 | 1.19 | 26.27 |
| C-C | 0.60 | 23.7 | 1.71 | 28.89 |

Examples 12-14 and Comparative Example D

Curable formulations were prepared by combining all ingredients and thoroughly mixing them for each Example and Comparative Example. Table 6 below summarizes the ingredients used and their amounts (in grams) for each of the resulting formulations. Catalyst Composition No. 1 was used as the catalyst composition for Example 12, DBU alone was used as the catalyst composition for Comparative Example D, and DBU was mixed with zinc bis(2-ethylhexanoate) (in the amounts shown in Table 6) to form the catalyst compositions for Examples 13 and 14.

TABLE 6

Curable Formulation

| Example No. | Solvent Heptane (g) | Solvent Toluene (g) | SYL-OFF™ 2792 (g) | SYL-OFF™ 7048 (g) | Catalyst Composition No. 1 (g) | DBU (g)/ Zinc Bis (2-ethyl-hexanoate) (g) | Acetic Anhydride Stabilizer (g) |
|---|---|---|---|---|---|---|---|
| 12 | 8.47 | 8.47 | 7.81 | 0.2 | 0.2 | | 0.05 |
| C-D | 8.47 | 8.47 | 7.81 | 0.2 | | 0.2/0.0 | 0.05 |
| 13 | 16.94 | 16.94 | 15.62 | 0.4 | | 0.1/0.3 | 0.1 |
| 14 | 16.99 | 16.99 | 15.62 | 0.4 | | 0.1/0.3 | |

The curable formulations were aged for 1 hour and were then coated on the primed side of a 50 micrometer thick polyester terephthalate (PET) film (obtained from Mitsubishi Polyester Film, Greer, S.C., under the trade designation Hostaphan™ 3 SAB, referred to hereinafter as 3 SAB PET film, which has one side chemically treated or primed to improve the adhesion of silicone coatings) using a number #4 Meyer rod. The resulting coatings were cured at 80° C. for 2 minutes in an oven equipped with solvent exhaust. The resulting cured samples were then tested for their release liner adhesion and liner-side peel adhesion (readhesion) using the methods described above except that, instead of coating the samples with an acrylic radiation-sensitive syrup (which was then converted to a pressure sensitive adhesive layer), the samples were laminated to the following commercially available adhesive tapes:

Tape A was an acrylic pressure-sensitive adhesive tape comprising a polypropylene backing commercially available from 3M Company, St. Paul, Minn. under the trade designation Scotch™ Magic™ Tape 810.

Tape B was an acrylic pressure-sensitive adhesive tape comprising a polypropylene backing commercially available from 3M Company, St. Paul, Minn. under the trade designation Scotch™ Book Tape 845.

Tape C was a rubber adhesive tape comprising a crepe paper backing commercially available from 3M Company, St. Paul, Minn. under the trade designation Scotch™ High-Performance Masking Tape 232.

Before release liner adhesion and liner-side peel adhesion (readhesion) tests were carried out, the resulting laminates were aged for three days at room temperature (RT; 23° C.) or at 70° C. Table 7 below summarizes the test data for each of the aged laminates.

TABLE 7

| Example No. | Tape | Release Liner Adhesion (N/dm) Aging at 23° C. | Release Liner Adhesion (N/dm) Aging at 70° C. | Readhesion (N/dm) Aging at 23° C. | Readhesion (N/dm) Aging at 70° C. |
|---|---|---|---|---|---|
| 12 | Tape A | 0.19 | 0.49 | 24.78 | 42.31 |
|  | Tape B | 0.26 | 0.54 | 69.74 | 70.79 |
|  | Tape C | 0.44 | 2.87 | 88.02 | 102.14 |
| C-D | Tape A | 0.14 | 0.14 | 39.31 | 45.62 |
|  | Tape B | 0.19 | 0.19 | 57.99 | 58.66 |
|  | Tape C | 0.17 | 0.48 | 84.30 | 95.83 |
| 13 | Tape A | 0.26 | 0.76 | 34.06 | 46.08 |
|  | Tape B | 0.31 | 0.91 | 78.15 | 78.41 |
|  | Tape C | 1.00 | 4.81 | 91.19 | 103.93 |
| 14 | Tape A | 0.2 | 0.32 | 19.24 | 34.80 |
|  | Tape B | 0.27 | 0.48 | 41.98 | 56.04 |
|  | Tape C | 0.43 | 4.31 | 86.97 | 97.91 |

Examples 15-24 and Comparative Examples E-F

Curable formulations were prepared by mixing SYL-OFF™ 292 in a heptane-MEK solvent mixture and adding a desired amount of various catalyst compositions. The curable formulations are summarized in Table 8 below. The curable formulations were thoroughly mixed and observed for outgassing. Then each formulation was coated on the primed side of a 50 micrometer thick polyester terephthalate (PET) film (obtained from Mitsubishi Polyester Film, Greer, S.C., under the trade designation Hostaphan™ 3 SAB) with a #4 Meyer bar. The resulting coatings were cured at various temperatures for 2 minutes in an oven equipped with solvent exhaust. The degree of cure achieved and attachment to the film substrate were evaluated by rubbing the cured coatings with a thumb. A "smear" indicated little or no cure; "rub off" indicated cure but poor anchorage; and "good" indicated cure and anchorage. Table 9 below summarizes the cure behavior of the formulations.

TABLE 8

| Example No. | SYL-OFF™ 292 (g) | Solvent Heptane (g) | Solvent MEK (g) | Catalyst Composition Type | Catalyst Composition Amount (g) |
|---|---|---|---|---|---|
| 15 | 7.81 | 13.59 | 3.4 | No. 3 | 0.20 |
| 16 | 1.88 | 18.38 | 4.6 | No. 6 | 0.15 |
| 17 | 7.81 | 13.59 | 3.4 | No. 6 | 0.20 |
| 18 | 7.81 | 13.67 | 3.42 | No. 6 | 0.10 |
| 19 | 7.81 | 13.63 | 3.41 | No. 6 | 0.15 |
| 20 | 1.88 | 18.38 | 4.6 | No. 5 | 0.15 |
| 21 | 7.81 | 13.59 | 3.4 | No. 5 | 0.20 |

TABLE 8-continued

| Example No. | SYL-OFF™ 292 (g) | Solvent | | Catalyst Composition | |
|---|---|---|---|---|---|
| | | Heptane (g) | MEK (g) | Type | Amount (g) |
| 22 | 7.81 | 13.67 | 3.42 | No. 5 | 0.10 |
| 23 | 7.81 | 13.63 | 3.41 | No. 5 | 0.15 |
| 24 | 7.81 | 13.59 | 3.4 | No. 7 | 0.20 |
| C-E | 7.81 | 13.59 | 3.4 | Trimethylborate | 0.20 |
| C-F | 7.81 | 13.59 | 3.4 | Triethylborate | 0.20 |

TABLE 9

| Example No. | Catalyst Composition | Outgas (Yes/No) | Rub Test After Cure @ Temperature (° C.) | | | | |
|---|---|---|---|---|---|---|---|
| | | | 23 | 50 | 65 | 70 | 100 |
| 15 | No. 3 | No* | | | | | Rub Off |
| 16 | No. 6 | No | | Good | | Good | |
| 17 | No. 6 | No* | | Good | | | |
| 18 | No. 6 | No* | | Smear | | | |
| 19 | No. 6 | No* | | Smear | | | |
| 20 | No. 5 | No* | | Good | | | |
| 21 | No. 5 | No* | | Good | | | |
| 22 | No. 5 | No* | | Good | | | |
| 23 | No. 5 | No* | | Good | | | |
| 24 | No. 7 | Yes | Rub Off | Rub Off | | | |
| C-E | Trimethylborate | No* | | Smear | | | |
| C-F | Triethylborate | No | | Smear | | | |

*Only an occasional bubble was seen over a 30 minute period.

The resulting cured samples were then tested for percent extractable silicone, release liner adhesion, and liner-side peel adhesion (readhesion) using the methods described above except that, instead of coating the cured samples with an acrylic radiation-sensitive syrup (which was then converted to a pressure sensitive adhesive layer), the cured samples were laminated to Tape A as described for Example 12 above. The resulting laminates were not aged prior to testing. Table 10 below summarizes the test data obtained for the laminates.

TABLE 10

| Example No. | Percent Extractable Silicone | Release Liner Adhesion (N/dm) | Readhesion (N/dm) |
|---|---|---|---|
| 16 | 14.5 | 0.16 | 19.70 |
| 17 | 13.2 | 0.10 | 18.50 |
| 20 | 10.8 | 0.19 | 21.12 |
| 21 | 11.0 | 0.10 | 20.47 |
| 22 | 18.6 | 0.09 | 21.01 |
| 23 | 21.0 | | |
| 24 | | 0.14 | 20.69 |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows.

We claim:
1. A curable composition comprising
(a) at least one polyorganosiloxane, fluorinated polyorganosiloxane, or combination thereof comprising reactive silane functionality comprising at least two hydroxysilyl moieties;
(b) at least one polyorganosiloxane, fluorinated polyorganosiloxane, or combination thereof comprising reactive silane functionality comprising at least two hydrosilyl moieties; and
(c) a catalyst composition comprising (1) at least one base selected from amidines, guanidines, phosphazenes, proazaphosphatranes, and combinations thereof, and (2) at least one Lewis acid;
wherein at least one of said components (a) and (b) has an average reactive silane functionality of at least three; and wherein said curable composition further comprises at least one carboxylic acid, at least one carboxylic acid anhydride, or a combination thereof.

2. The composition of claim 1, wherein said components (a) and (b) each comprise at least one polyorganosiloxane; and/or wherein said component (a) is hydroxyl-endblocked.

3. The composition of claim 1, wherein said component (a) is selected from polysiloxanes that are represented by the following general formula:

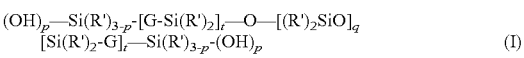

$$(OH)_p\text{—}Si(R')_{3-p}\text{-}[G\text{-}Si(R')_2]_t\text{—}O\text{—}[(R')_2SiO]_q\\ [Si(R')_2\text{-}G]_t\text{—}Si(R')_{3-p}\text{-}(OH)_p \quad (I)$$

wherein each p is independently an integer of 1, 2, or 3; each G is independently a divalent linking group; each R' is independently selected from alkyl, alkenyl, fluoroalkyl, aryl, fluoroaryl, cycloalkyl, fluorocycloalkyl, heteroalkyl, heterofluoroalkyl, heteroaryl, heterofluoroaryl, heterocycloalkyl, heterofluorocycloalkyl, and combinations thereof; q is an integer of 0 to 15,000; and each t is independently an integer of 0 or 1.

4. The composition of claim 1, wherein said component (b) has an average reactive silane functionality of at least three.

5. The composition of claim 1, wherein said component (b) is selected from polysiloxanes that are represented by the following general formula:

$$R'_2R''SiO(R'_2SiO)_r(HR'SiO)_sSiR''R'_2 \quad (II)$$

wherein each R' is independently selected from alkyl, alkenyl, fluoroalkyl, aryl, fluoroaryl, cycloalkyl, fluorocycloalkyl, heteroalkyl, heterofluoroalkyl, heteroaryl, heterofluoroaryl, heterocycloalkyl, heterofluorocycloalkyl, and combinations thereof; each R" is independently hydrogen or R'; r is an integer of 0 to 150; and s is an integer of 2 to 150.

6. The composition of claim 1, wherein said base of component (c) is selected from
(1) amidine compounds that are represented by the following general formula:

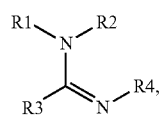

(2) guanidine compounds that are represented by the following general formula:

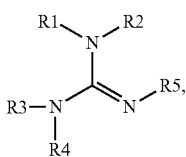

(3) phosphazene compounds that are represented by the following general formula:

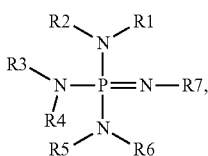

(4) proazaphosphatrane compounds that are represented by the following general formula:

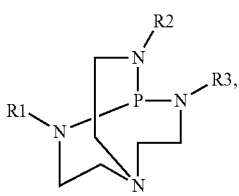

and combinations thereof;
wherein R1, R2, R3, R4, R5, R6, and R7 are each independently selected from hydrogen, monovalent organic groups, monovalent heteroorganic groups, and combinations thereof; and wherein any two or more of R1, R2, R3, R4, R5, R6, and R7 of said amidine, guanidine, and/or phosphazene compounds optionally can be bonded together to form a ring structure.

7. The composition of claim 6, wherein said base of component (c) is selected from amidine compounds, guanidine compounds, phosphazene compounds, and combinations thereof that each comprise at least one said ring structure.

8. The composition of claim 1, wherein said base of component (c) is selected from 1,2-dimethyl-1,4,5,6-tetrahydropyrimidine, 1,8-diazabicyclo[5.4.0]-7-undecene (DBU), 1,5-diazabicyclo[4.3.0]-5-nonene (DBN), 1,5,7-triazabicyclo[4.4.0]dec-5-ene (TBD), 7-methyl-1,5,7-triazabicyclo[4.4.0]dec-5-ene (MTBD), 2-tert-butyl-1,1,3,3-tetramethylguanidine, 2-tert-butylimino-2-diethylamino-1,3-dimethylperhydro-1,3,2-diazaphosphorine, phosphazene base $P_1$-t-Bu-tris(tetramethylene), phosphazene base $P_4$-t-Bu, 2,8,9-triisopropyl-2,5,8,9-tetraaza-1-phosphabicyclo[3.3.3]undecane, and combinations thereof.

9. The composition of claim 1, wherein said base is selected from amidines, guanidines, and combinations thereof.

10. The composition of claim 1, wherein said Lewis acid is selected from metal salts, trialkylborates, triarylborates, and combinations thereof.

11. The composition of claim 10, wherein said metal salts are metal salts of at least one organic acid.

12. The composition of claim 11, wherein said metal salts of at least one organic acid are metal carboxylates.

13. The composition of claim 10, wherein said metal is selected from zinc, iron, copper, bismuth, aluminum, magnesium, and combinations thereof.

14. The composition of claim 1, wherein said Lewis acid is at least one metal salt; or wherein said Lewis acid is at least one trialkylborate.

15. The composition of claim 1, wherein said Lewis acid is selected from the butryrate (butanoate), octanoate, neodecanoate, and ethylhexanoate salts of zinc, bismuth, aluminum, magnesium, and combinations thereof; trimethylborate; triethylborate; triisopropylborate; triphenylborate; tri(substituted phenyl)borates; and combinations thereof.

16. The composition of claim 1, wherein said composition is a tin catalyst-free composition; wherein said composition is in the form of an emulsion; and/or wherein said composition has been cured.

17. A coating process comprising
 (a) providing the curable polysiloxane composition of claim 1;
 (b) providing at least one substrate having at least one major surface;
 (c) applying said curable polysiloxane composition to at least a portion of at least one said major surface of said substrate; and
 (d) allowing or inducing said curable polysiloxane composition to cure to form a coating.

18. An article comprising at least one substrate having at least one major surface, said substrate bearing, on at least a portion of at least one said major surface, a coating prepared by the coating process of claim 17.

19. An article comprising a cured curable composition, wherein the curable composition is the composition of claim 1.

20. A curable composition comprising
 (a) at least one polyorganosiloxane, fluorinated polyorganosiloxane, or combination thereof that is hydroxyl-endblocked;
 (b) at least one polyorganosiloxane, fluorinated polyorganosiloxane, or combination thereof comprising at least three hydrosilyl moieties; and
 (c) a catalyst composition comprising (1) at least one base selected from 1,2-dimethyl-1,4,5,6-tetrahydropyrimidine, 1,8-diazabicyclo[5.4.0]-7-undecene (DBU), 1,5-diazabicyclo[4.3.0]-5-nonene (DBN), 1,5,7-triazabicyclo[4.4.0]dec-5-ene (TBD), 7-methyl-1,5,7-triazabicyclo[4.4.0]dec-5-ene (MTBD), 2-tert-butyl-1,1,3,3-tetramethylguanidine, and combinations thereof, and (2) at least one Lewis acid selected from metal salts, trialkylborates, triarylborates, and combinations thereof; and
wherein said curable composition further comprises at least one carboxylic acid, at least one carboxylic acid anhydride, or a combination thereof.

* * * * *

UNITED STATES PATENT AND TRADEMARK OFFICE
CERTIFICATE OF CORRECTION

PATENT NO. : 9,006,357 B2
APPLICATION NO. : 14/368332
DATED : April 14, 2015
INVENTOR(S) : Yu Yang et al.

It is certified that error appears in the above-identified patent and that said Letters Patent is hereby corrected as shown below:

On The Title Page, Item (56)

Page 2, Column 2 (Other Publications)
Line 13, Delete "[(DBU-H)(PbI$_3$)]$_n$:" and insert -- [(DBU-H)(PbI$_3$)]$_n$:" --, therefor.

In The Specification

Column 12

Lines 47-53 (Approx.), Delete " 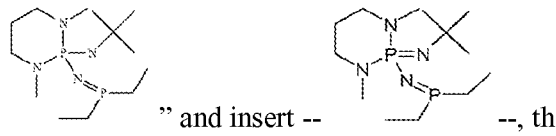 " and insert -- -- , therefor.

Column 16
Line 39, Delete "butiyrate" and insert -- butyrate --, therefor.

Column 16
Line 42, Delete "butiyrate" and insert -- butyrate --, therefor.

Column 25 (Table 1)
Line 5 (Approx.), Delete "MTBC" and insert -- MTBD --, therefor.

In The Claims

Column 38
Line 14, In Claim 15, delete "butryrate" and insert -- butyrate --, therefor.

Signed and Sealed this
Ninth Day of February, 2016

Michelle K. Lee
*Director of the United States Patent and Trademark Office*